(12) United States Patent
Yamada et al.

(10) Patent No.: US 6,341,637 B1
(45) Date of Patent: *Jan. 29, 2002

(54) TUBE CONNECTING APPARATUS

(75) Inventors: Yoshiyuki Yamada, Kasugai; Hiroaki Sano; Yoshiro Suzuki, both of Nakakoma-gun, all of (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/458,012

(22) Filed: Dec. 10, 1999

Related U.S. Application Data

(62) Division of application No. 08/987,044, filed on Dec. 10, 1997, now Pat. No. 6,026,882.

(30) Foreign Application Priority Data

Dec. 11, 1996 (JP) ................................. 8-330579
Jul. 10, 1997 (JP) ................................. 9-184803

(51) Int. Cl.[7] ............................................. A61M 39/00

(52) U.S. Cl. ........................ 156/433; 156/499; 156/503

(58) Field of Search ................................. 156/158, 159, 156/228, 266, 304.2, 304.6, 308.2, 433, 499, 503

(56) References Cited

U.S. PATENT DOCUMENTS

| 4,610,670 A | 9/1986 | Spencer ........................ 694/29 |
| 5,141,592 A | 8/1992 | Shaposka et al. ............ 156/515 |
| 5,248,359 A | 9/1993 | Shaposka et al. ............ 156/158 |

FOREIGN PATENT DOCUMENTS

| EP | 0 507 321 | 10/1992 |
| EP | 0 667 226 | 8/1995 |
| EP | 0 739 672 | 10/1996 |
| EP | 0 778 123 | 6/1997 |
| JP | 9-154920 | 6/1997 |

*Primary Examiner*—Sam Chuan Yao
(74) *Attorney, Agent, or Firm*—Finnegan, Henderson, Farabow, Garrett & Dunner, L.L.P.

(57) ABSTRACT

A tube connecting apparatus for grasping and heating to melt and alternately connect the cut ends of a plurality of tubes is disclosed. A first tube holder and a second tube holder for grasping the tubes are provided with a pair of clamps having holding portions for holding a plurality of tubes; each of the pair of clamps being moved into contact with, and away from, each other. One or both of the holding portions of the first tube holder and the second tube holder are formed of semi-circular separatable members and having a symmetry of rotation in relation to the center of the rotating axis, and have a grasping means for moving into contact with, and away from, the pair of clamps and have a rotating means for rotating the semi-circular holding portions of one or both of the first tube holder and the second tube holder.

5 Claims, 21 Drawing Sheets

TUBE CONNECTING APPARATUS

This division of application Ser. No. 08/987,044, filed Dec. 10, 1997 now U.S. Pat. No. 6,026,882 of which is incorporated herein by reference.

BACKGROUND OF THE INVENTION

1. Field of the Invention

The present invention relates to a tube connecting apparatus for heating and melting to cut flexible tubes and connecting the tubes by mutually welding the cut end faces thereof.

2. Description of the Related Art

According to a conventional tube connecting apparatus, two tubes, for instance, to be connected are held in parallel with each other and a cutting plate comprising a plate-like heating element is moved as if to cross the tubes, thereby heating and melting to cut the tubes. The tubes thus held are rotated so that the cut ends will slide on the cutting plate, and then the melted cut ends of the tubes are connected with each other by the withdrawal of the cutting plate.

A conventional example of a tube connecting apparatus having the above-described function, particularly a holder for holding tubes, will hereinafter be briefly explained. FIG. 28 is a perspective illustration showing a holder in use in a conventional tube connecting apparatus.

The tube connecting apparatus of the conventional example comprises a fixed tube holder 201 which is fixedly secured at all times, and a movable tube holder 202 which is rotatable and movable in the axial direction of tubes. The fixed tube holder 201 and the movable tube holder 202 are provided with grooves 231 and 241 in holder blocks 203 and 204 in which tubes 205 and 206 can be mounted. On the holder blocks 203 and 204, covers 207 and 208 are rotatably attached by hinges. Therefore, with the rotation of the covers 207 and 208, the grooves 231 and 241 of the holder blocks 203 and 204 are opened and closed. The fixed tube holder 201 and the movable tube holder 202 are provided with a locking mechanism. The lock mechanism is composed of engaging pawls 271 and 281 protrusively provided on the covers 207 and 208, and engaging holes 232 and 242 provided by drilling in the holder blocks 203 and 204 which engage with the engaging pawls 271 and 281.

The movable tube holder 202 is set a specific distance off the fixed tube holder 201, and the grooves 231 and 241 are positioned so as to be aligned on one line.

The movable tube holder 202 is provided with rotating means for rotating itself. This rotating means is formed such that the forward end of a crankshaft connected to a driving shaft of a motor 210 is secured to the holder block 204 of the movable tube holder 202. On the extension M of the driving shaft of the motor 210, the grooves 231 and 241 formed in the holder blocks 203 and 204 of the fixed tube holder 201 and the movable tube holder 202 are extendedly present, so as to be located on, or in the vicinity of, the tubes 205 and 206 which are charged one over the other within the grooves 231 and 241.

In the case of the conventional tube connecting apparatus of the above-described constitution, first the grooves 231 and 241 are opened by the user of the apparatus by turning the covers 207 and 208 upwards from the holder blocks 203 and 204 of the fixed tube holder 201 and the movable tube holder 202. Then, the tubes 205 and 206 are set one over the other in the grooves 231 and 241 thus opened upwards. Subsequently the covers 207 and 208 are turned downwards to close the grooves 231 and 241 with the tubes 205 and 206 thus set, and are held down until the engaging pawls 271 and 281 of the covers 207 and 208 are firmly engaged with the engaging holes 232 and 242 formed in the holder blocks 203 and 204.

Subsequently, after thus setting the tubes 205 and 206 on the tube connecting apparatus, the user depresses an unillustrated starting switch to ON, thereby connecting the cut ends of these tubes 205 and 206 by the above-described operation.

That is, when the switch is depressed to ON, an unillustrated cutting plate travels between the fixed tube holder 201 and the movable tube holder 202 to cut the tubes 205 and 206. After the cutting of the tubes 205 and 206, the movable tube holder 202 is turned 180 degrees up and down through the crankshaft 211 by turning power of the motor 210. Then, when the cutting plate is withdrawn, the movable tube holder 202 is axially moved by unillustrated moving means by the same amount as the thickness of the cutting plate towards the fixed tube holder 201, melting to mutually connect the cut ends of the tubes 205 and 206. At this time, as the tube holder 202 has been turned 180 degrees, the cover 208 faces down and the holder block 204 faces up.

Subsequently, the user opens the groove 231 by turning the cover 207 upwards from the holder block 203 of the fixed tube holder 201.

Thereafter, with the starting switch pressed to ON, the movable tube holder 202 is turned 180 degrees by the turning power from the motor 210 through the crankshaft 211. Then, as the cover 208 of the movable tube holder 202 faces up, the groove 241 is opened by turning the cover 208 upwards from the holder block 204, and the tubes thus connected are taken out.

The conventional tube connecting apparatus, however, has the following problems.

In the above-described conventional tube connecting apparatus, as the movable tube holder 202 has turned 180 degrees from the state before jointing, the cover 208 can not turn from the holder block 204 and accordingly the tubes can not be taken out after the tubes 205 and 206 are cut and jointed.

To take out the jointed tubes, the groove 231 is opened in advance by turning the cover 207 upwards from the holder block 203 of the fixed tube holder 201. Next, it is necessary to open the groove 241 of the holder block 204, after the cover 208 turns to face up, by operating the starting switch to turn the connected tube 180 degrees, together with the movable tube holder 262, and then to turn the cover 208 further upwards, making operation complicated and requiring much time for pipe connection.

Furthermore, in the conventional tube connecting apparatus, as described above, the apparatus automatically cuts and connects the tubes 205 and 206; and therefore the user himself is required to carry out setting the tubes 205 and 206 to, and taking out the tubes from, the apparatus.

In this case, it becomes necessary to open and close the covers 207 and 208 together with the fixed tube holder 201 and the movable tube holder 202. However, in order to prevent connection error likely to be caused by misalignment of the tubes 205 and 206, there is provided lock means which comprises the engaging pawls 271 and 281 and the engaging holes 232 and 242. Therefore a power is needed to open and close the covers 207 and 208 when the user sets the tubes 205 and 206 on the fixed tube holder 201 and the movable tube holder 202. To open and close the covers 207 and 208, about 1.5 to 2 kgf finger tip pressure is required.

This degree of pressure is liable to be thought not so great a pressure for a physically sound person, who therefore can easily open and close the covers 207 and 208. However, the present apparatus is used for connecting a transfer tube connected with the abdominal cavity to a tube connected with a dialysis pack to supply for instance a dialysis solution into the abdominal cavity of a peritoneum dialysis patient. Therefore, it is quite an easy operation to the physically sound person to open and close the covers 207 and 208. However, it is a hard work to such a physically handicapped person as a peritoneum patient who is weak-sighted or has a low physical strength.

Furthermore, in the conventional tube connecting apparatus described above, the tubes 205 and 206 are set one over the other in the grooves 231 and 241 formed in the holder blocks 203 and 204; therefore, the lower tube in the grooves 231 and 241, if pulled first by mistake after connection, will be caught by the upper tube, resulting in such a disadvantage as twist or damage.

Furthermore, there also occurs such a problem that if the movable tube holder 202 holding the tubes 205 and 206 is turned, the tubes will twist around the motor 210 mounted outside of the movable tube holder 202 and also around the crankshaft 211 transmitting the power from the motor 210 to the holder block 204.

SUMMARY OF THE INVENTION

To cope with such problems or disadvantages stated above, it is an object of the present invention to provide a tube connecting apparatus which has lessened the user's burden in order to ensure easy handling, and also is capable of preventing interference between driving means and tubes.

To accomplish the above-mentioned object, the tube connecting apparatus of the present invention has the following constitution.

That is, the tube connecting apparatus of the present invention has a first tube holder and a second tube holder for holding a plurality of flexible tubes, and cutting means for heating and melting to cut the tubes between the first tube holder and the second tube holder while the tubes are as-held in the first tube holder and the second tube holder. Each of the first tube holder and the second tube holder has a holding portion for holding the aforesaid tubes, and grasping means driven so that the tube contact portions of the holding portion will contact, and be apart from, each other, to thereby grasp and release the tubes. One or both holding portions are separable into members having a rotation symmetry in relation to the center of the rotating axis, and are rotatably mounted by rotating means.

In the tube connecting apparatus of the present invention of the above-described constitution, the user set tubes in the holding portion formed in the contact portion between a pair of clamps of the first tube holder and the second tube holder which are disposed apart. Thereafter, the pair of clamps grasp the tubes in contact by the grasping means in the holding portion, and then the cutting means inserts between the first tube holder and the second tube holder to heat and melt to cut the tubes. Then, the holding portion is rotated by the aforesaid rotating means to turn the holding portion in which the tubes are grasped, thereby changing the positions of the tubes. Thus the cut ends of different tubes face each other through the cutting means. Thereafter, simultaneously with the withdrawal of the cutting means, the first tube holder and the second tube holder are brought closer to each other by the aforesaid adjusting means, thereby connecting the cut ends of the tubes. That is, the cut ends of different tubes are welded each other. Subsequently the pair of clamps of the first tube holder and the second tube holder are separated by the grasping means to allow the user to take out the connected tubes from the holding portion.

In the tube connecting apparatus of the present invention thus constituted, the tubes are reliably grasped in contact with a pair of holding portions operated by the grasping means; then the cutting means inserts between the first tube holder and the second tube holder to melt to cut the tubes. Thereafter the rotating means operates to turn the holding portion, to turn the holding portion grasping the tubes, thereby changing the tube positions. The cut ends of the different tubes face each other through the cutting means. Thereafter, simultaneously with the withdrawal of the cutting means, the first tube holder and the second tube holder are moved close to each other by the adjusting means, thus connected to each other. After thus welding the cut ends of the different tubes each other, the pair of holding portions of the first tube holder and the second tube holder are apart from again by grasping means.

In the meantime, for using the tube connecting apparatus, at least two tubes supported by the supporting means are moved to the holding position between the holding portions of the first tube holder and the second tube holder. The user, therefore, is required just to set the tubes to be connected on the supporting means outside of the grasping area of the holding portions within which the holding portions move, and to take the connected tubes out of the supporting means.

The tube connecting apparatus of the present invention has the following characteristic that the first tube holder and the second tube holder have holding portions for holding a plurality of tubes previously stated; one or both of the holding portions are separated into rotatable members having a rotation symmetry and are connected with a grasping means driven to move the holding portions into contact with, and away from, each other, and are connected with a rotating means for rotating one or both of the holding portions which are separated into the above-mentioned members of rotation symmetry, and have a supporting means for supporting the above-described at least two tubes together and moving these tubes to inside of the grasping area of the holding portions from outside of the grasping area of the holding portions.

In the tube connecting apparatus of the present invention, since it is unnecessary to open and close the cover when setting the tubes on the apparatus, the apparatus has become easier to handle with less burden on the user.

Furthermore, in the tube connecting apparatus of the present invention, a series of such operations as grasping, cutting, turning, connecting, and then releasing of grasped tubes are automatically carried out by control means. It, therefore, has become easy to handle the apparatus with reduced user's burden.

Other objects, together with the foregoing, are attained in the embodiments described in the following description and illustrated in the accompanying drawings.

DESCRIPTION OF THE PREFERRED EMBODIMENTS

Figure 1:
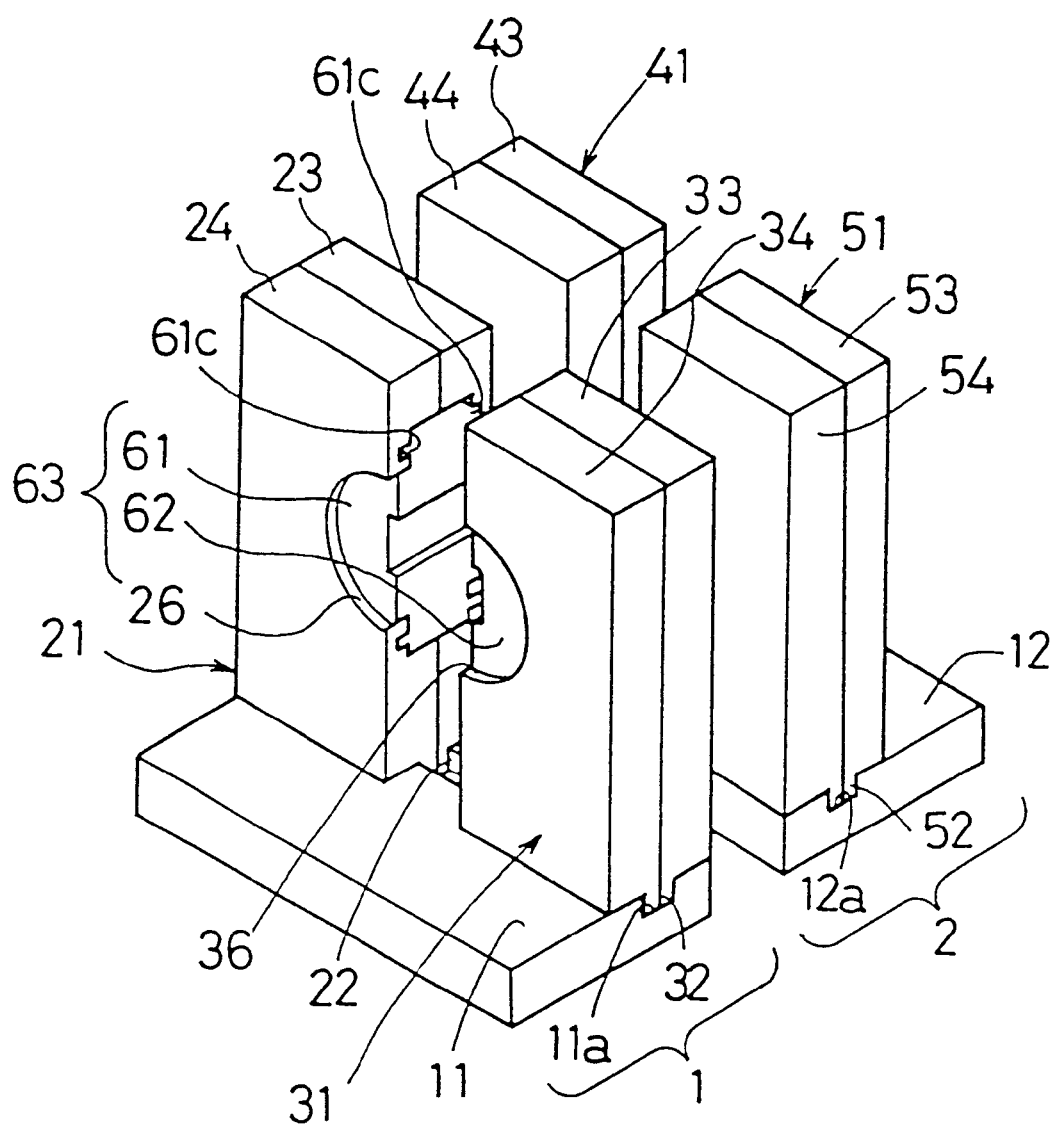
FIG. 1 is an external perspective illustration showing a major portion of one embodiment of a tube connecting apparatus of the present invention.

Next, the first embodiment of a tube connecting apparatus of the present invention will be explained with reference to the accompanying drawings. FIG. 1 is an exterior perspective illustration showing a major portion of the tube connecting apparatus of the present embodiment. The tube connecting apparatus comprises the first tube holder 1 and the second tube holder 2, which are engaged with an unillustrated body. In the first tube holder 1 and the second tube holder 2, fixed clamps 21 and 41 are fixedly mounted on bases 11 and 12; and movable clamps 31 and 51 movable to, and away from, the fixed clamps 21 and 41 are mounted. On the bases 11 and 12 are formed rail grooves 11a and 12a. On the bottom end of the fixed clamps 21 and 41 and the movable clamps 31 and 51 are formed projecting portions 22, 32, 42 and 52 which are engaged with the rail grooves 11a and 12a. With the projections 22, 32, 42 and 52 engaged with the rail grooves 11a and 12a, the fixed clamps 21 and 41 are fixed on the bases 11 and 12 to limit their movement; and the movable clamps 31 and 51 are so mounted as to be movable along the rail grooves 11a and 12a.

Figure 2:
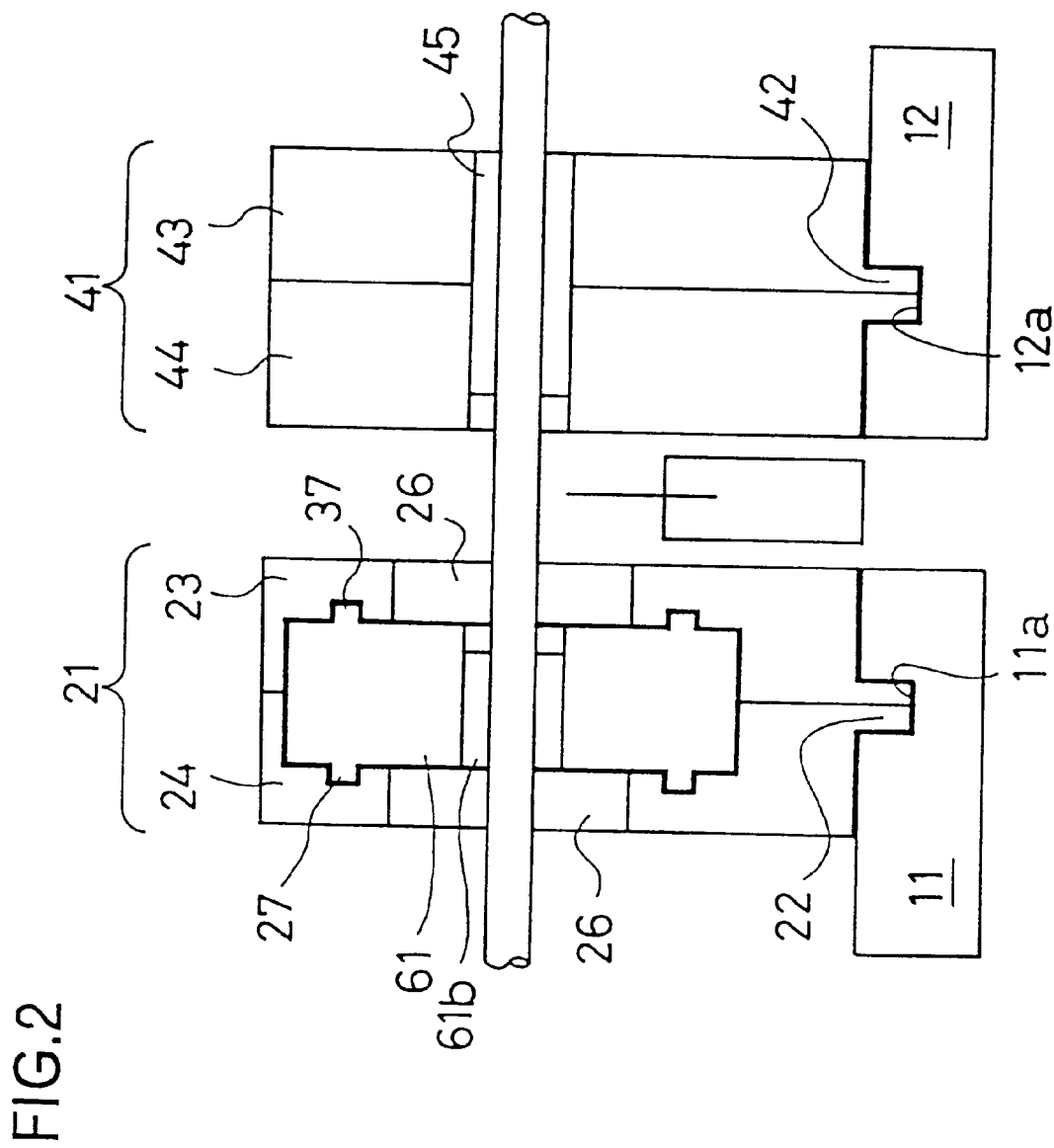
FIG. 2 is a front view showing contact surfaces of fixed clamps 21 and 41 of a first tube holder 1 and a second tube holder 2.
Figure 3:
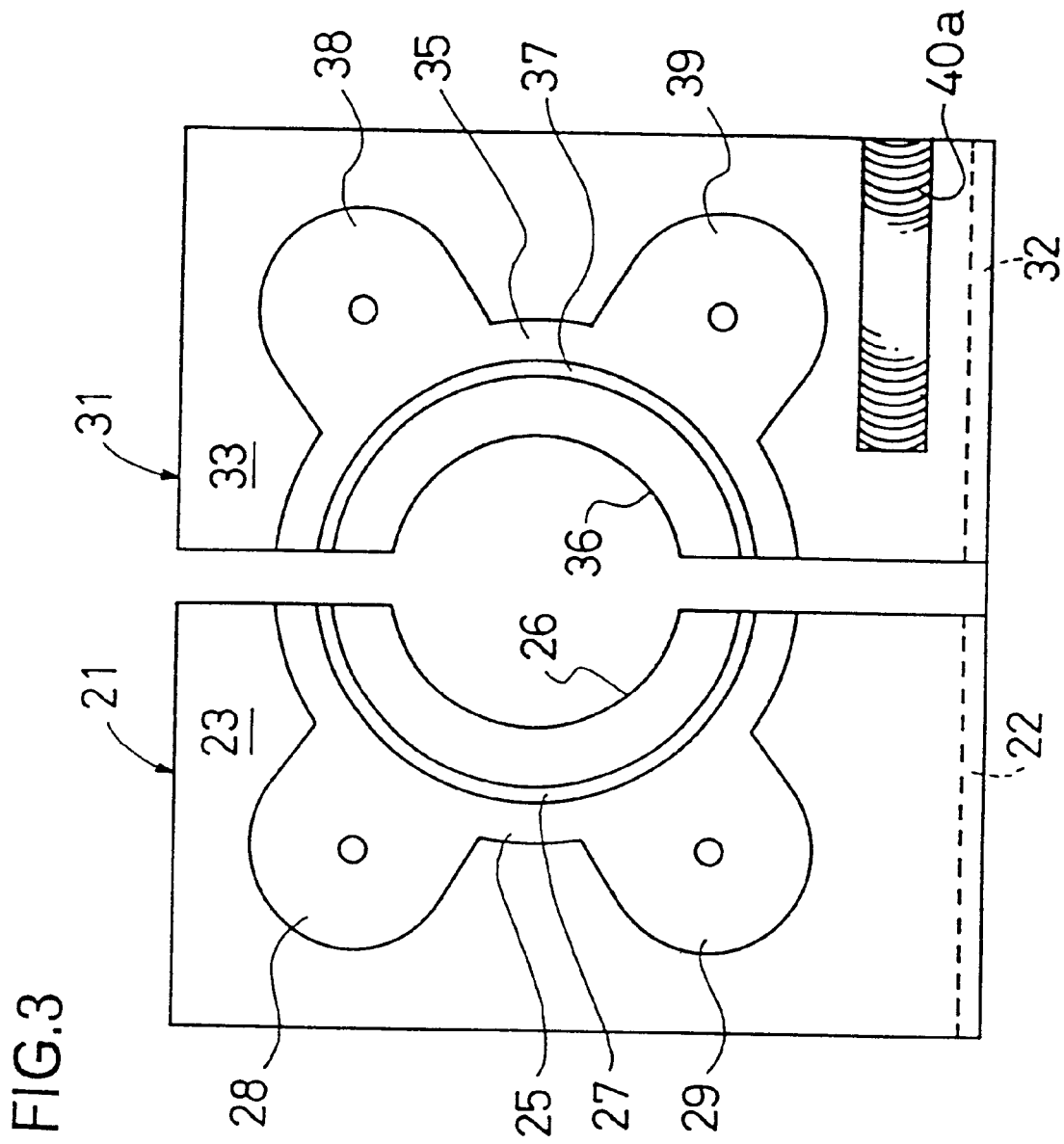
FIG. 3 is a vertical cross sectional view of a fixed clamp 21 and a movable clamp 31 of the first tube holder 1.

In the present embodiment, the first tube holder 1 has a later-described rotating mechanism, and the second tube holder 2 is not provided with such a rotating mechanism. FIG. 2 is a front view showing the contact surfaces of the fixed clamps 21 and 41 of the first tube holder 1 and the second tube holder 2. And FIG. 3 is a view showing the vertical portions of the fixed clamp 21 and the movable clamp 31 of the first tube holder 1.

The fixed clamp 21 and the movable clamp 31 of the first tube holder 1 comprise a pair of cover members 23 and 24 and a pair of cover members 33 and 34, which form one block as shown in FIG. 1. The cover members 23 and 24 and the cover members 33 and 34 are of a similar shape and symmetrical. The constitution of the cover members 23 and 33 on one side shown in FIG. 3 will be explained in detail. The cover members 23 and 33 are formed of a plate of specific thickness as shown, and the projections 22 and 32 are formed on the bottom end.

Above the projections 22 and 32 are formed rotor mounting portions 25 and 35 in which semi-circular recesses are provided for mounting a clamp rotor 63 (shown in FIG. 1) as a holding portion consisting of a pair of semi-circular rotor pieces 61 and 62. At the center of the rotor mounting portions 25 and 35 are formed semi-circular cutouts 26 and 36 in such a form that the central part of the clamp rotor 63 will be exposed (FIG. 1). In the rotor mounting portions 25 and 35 are formed semi-circular peripheral (circumferential) rails 27 and 37. The peripheral rails 27 and 37 are U-grooves.

In the upper and lower positions of the cover members 23 and 33, recesses are formed as gear mounting portions 28, 29, 38 and 39 continuing to the outer periphery of the rotor mounting portions 25 and 35. Furthermore, in the lower part of the cover member 33 is formed a threaded groove 40a constituting a screw hole 40 in which an output shaft 74 of a later-described motor 73 is screwed.

Figure 4:
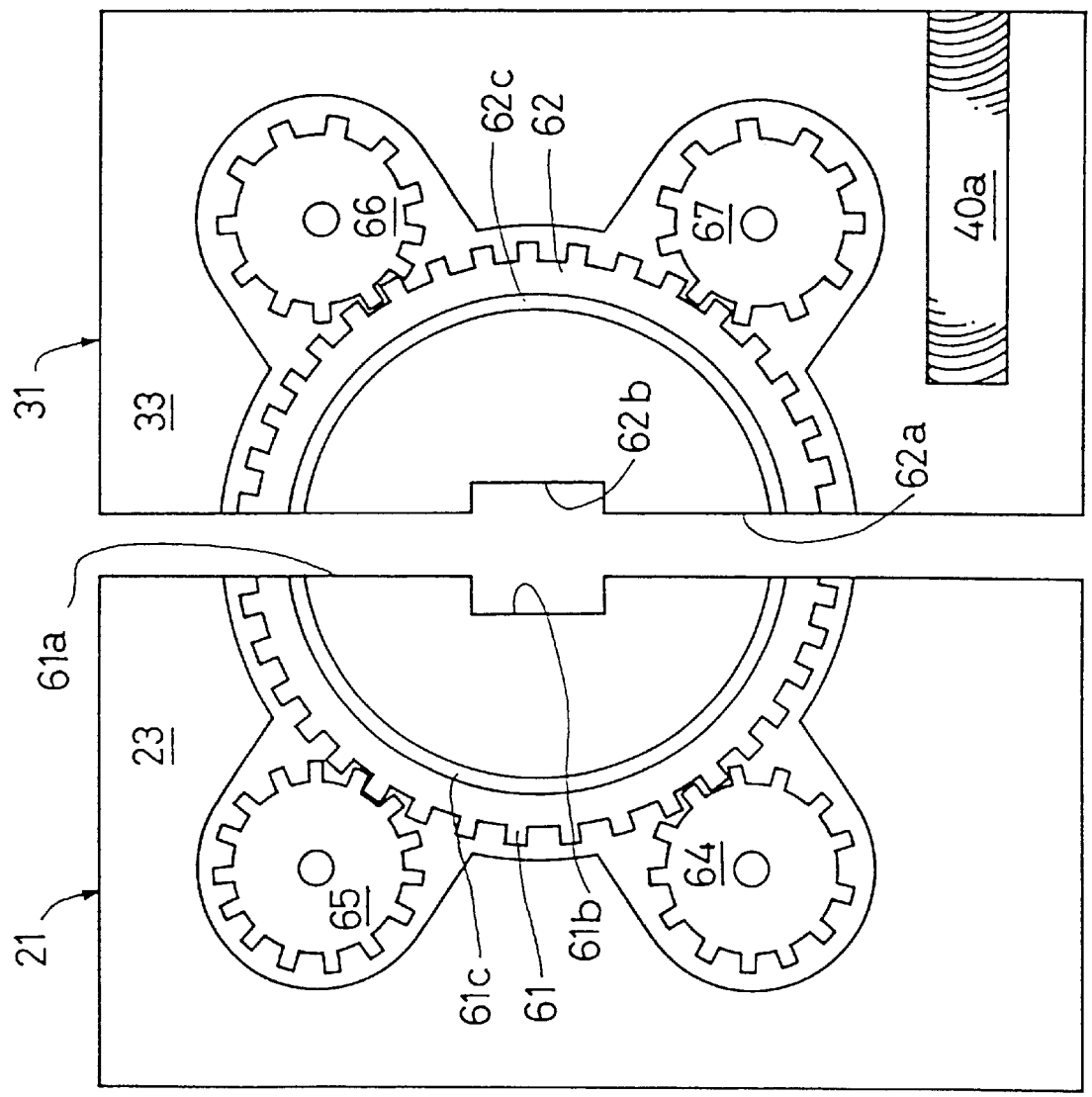
FIG. 4 is a view showing the fixed clamp 21 and the movable clamp 31 with a clamp rotor mounted in a cover member.

Next, FIG. 4 shows the state of the cover member of the above-described constitution in which the clamp rotor is mounted. The clamp rotor 63 shown in FIG. 1 which is mounted in the assembly of the cover members 23 and 24 and the cover members 33 and 34 is composed of a pair of semi-circular rotor pieces 61 and 62 as previously stated. On the periphery of the clamp rotor 63 are formed teeth, so that one gear is formed when the rotor pieces 61 and 62 are jointed. At the center of the clamp rotor 63 with the rotor pieces 61 and 62 jointed, that is, at the center of the contact surfaces 61a and 62a of the rotor pieces 61 and 62, grasping portions 61b and 62b of a U-shaped portion are formed. The grasping portions 61b and 62b are formed so deep that two tubes, when grasped horizontally by the grasping portions 61b and 62b, will be flattened to close in order to prevent the outflow of a liquid when cut.

On both sides of the rotor pieces 61 and 62 are formed peripheral projections 61c and 62c which fit in the peripheral rails 27, 27, 37 and 37 formed in the cover members 23, 24, 33 and 34.

In the meantime, gears 64, 65, 66 and 67 are rotatably supported and mounted into mesh with the rotor pieces 61 and 62, in the upper and lower positions, within the fixed clamp 21 and the movable clamp 31 of the first tube holder 1. Of these gears 64, 65, 66 and 67, the gear 64 mounted in the lower part of the cover members 23 and 24 which constitute the fixed clamp 21 functions as a drive gear coupled with the rotating axis of the driving motor.

The first tube holder 1 composed of the aforesaid component members is formed by mounting the rotor pieces 61 and 62 and the gears 64, 65, 66 and 67 to the cover members 23, 24, 33 and 34 of the fixed clamp 21 and the movable clamp 31. Subsequently, with the projections 22 and 32 engaged with the rail grooves 11a of the base 11 of the fixed clamp 21 and the movable clamp 31, the fixed clamp 21 is secured by fastening by screws the cover members 23 and 24, and tie movable clamp 31 is slidably engaged in the rail groove 11a.

Figure 5:
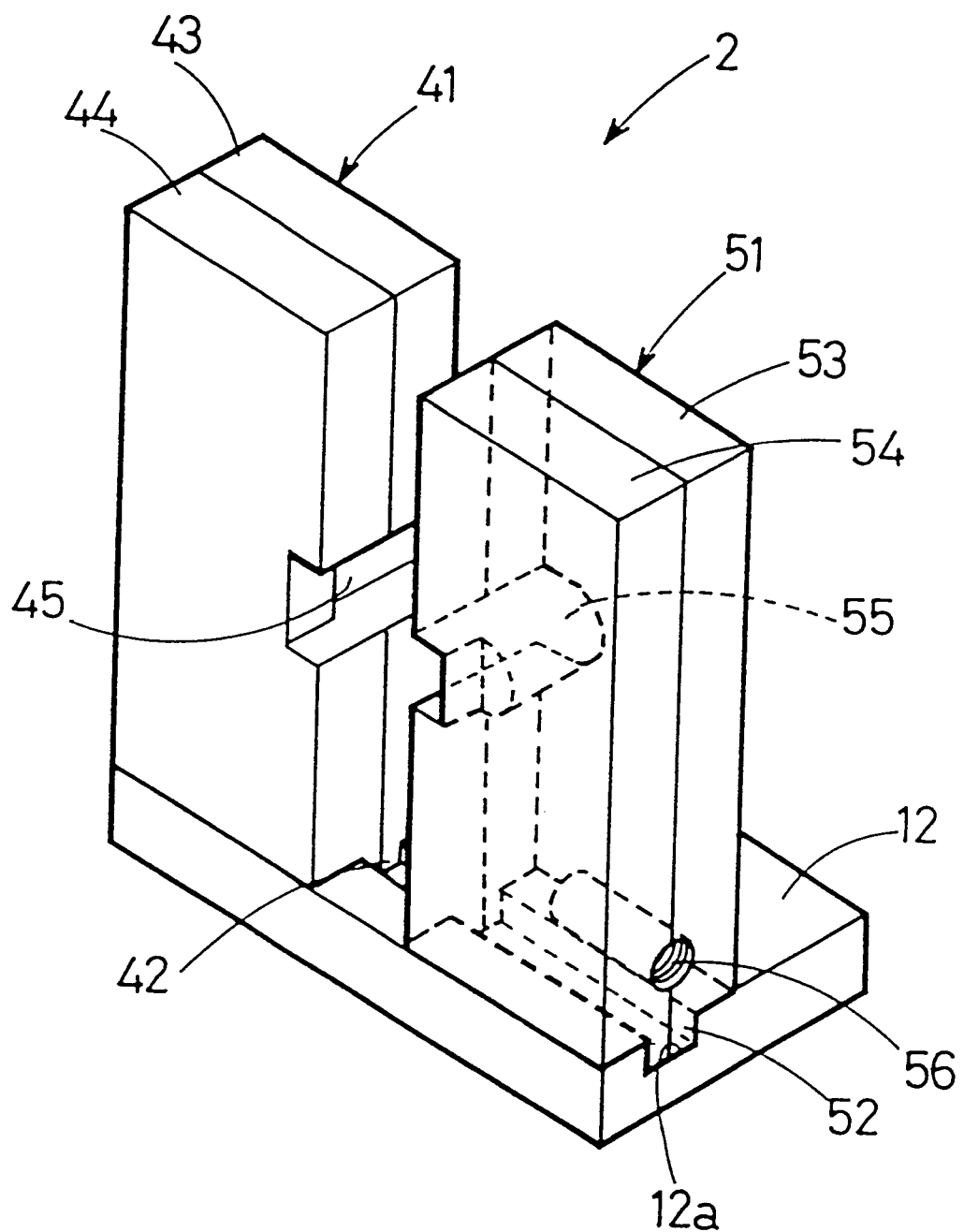
FIG. 5 is a perspective illustration showing the second tube holder 2.

Next, the second tube holder 2 will be explained. FIG. 5 is a perspective illustration showing the second tube holder 2.

The fixed clamp 41 and the movable clamp 51 which constitute the second tube holder 2 comprise a block formed by jointing the cover members 43 and 44 and the cover members 53 and 54 similarly to the first tube holder 1. The second tube holder 2, however, is not provided with a rotating mechanism as seen in the first tube holder 1. The cover members 43 and 44 and the cover members 53 and 54 have a mutually symmetrical shape. The shape is such that the projections 42 and 52 are formed on the bottom end of a plate of specific thickness; on the contact surface are formed grasping portions 45 and 55 to the same depth as the grasping portions 61b and 62b formed in the rotor pieces 61 and 62. That is, the grasping portions 45 and 55 are formed to the depth that two tubes, when grasped end to end, will be flattened.

The meeting ends of the grasping portions 61b and 62b and the grasping portions 45 and 55 are formed shallower, so that the tubes will be cut and connected in the as-flattened state in the midpoint, that is, in the cutting position, between the first tube holder 1 and the second tube holder 2. In the lower joint surface of the cover member 53 and. 54 is formed a screw hole 56 into which a later-described output shaft 76 of a motor 75 shown in FIG. 6 will be inserted.

The fixed clamp 41 and the movable clamp 51 consisting of the cover members 43 and 44 and the cover members 53 and 54 are constituted as follows: with the cover members 43 and 44 and the cover members 53 and 54 jointed, and with the projections 42 and 52 engaged with the rail grooves 12a of the base 12, the fixed clamp 41 is fixedly secured by fastening the cover members 43 and 44 by screws, while the movable clamp 51 is slidably engaged with the rail groove 12a.

Figure 6:
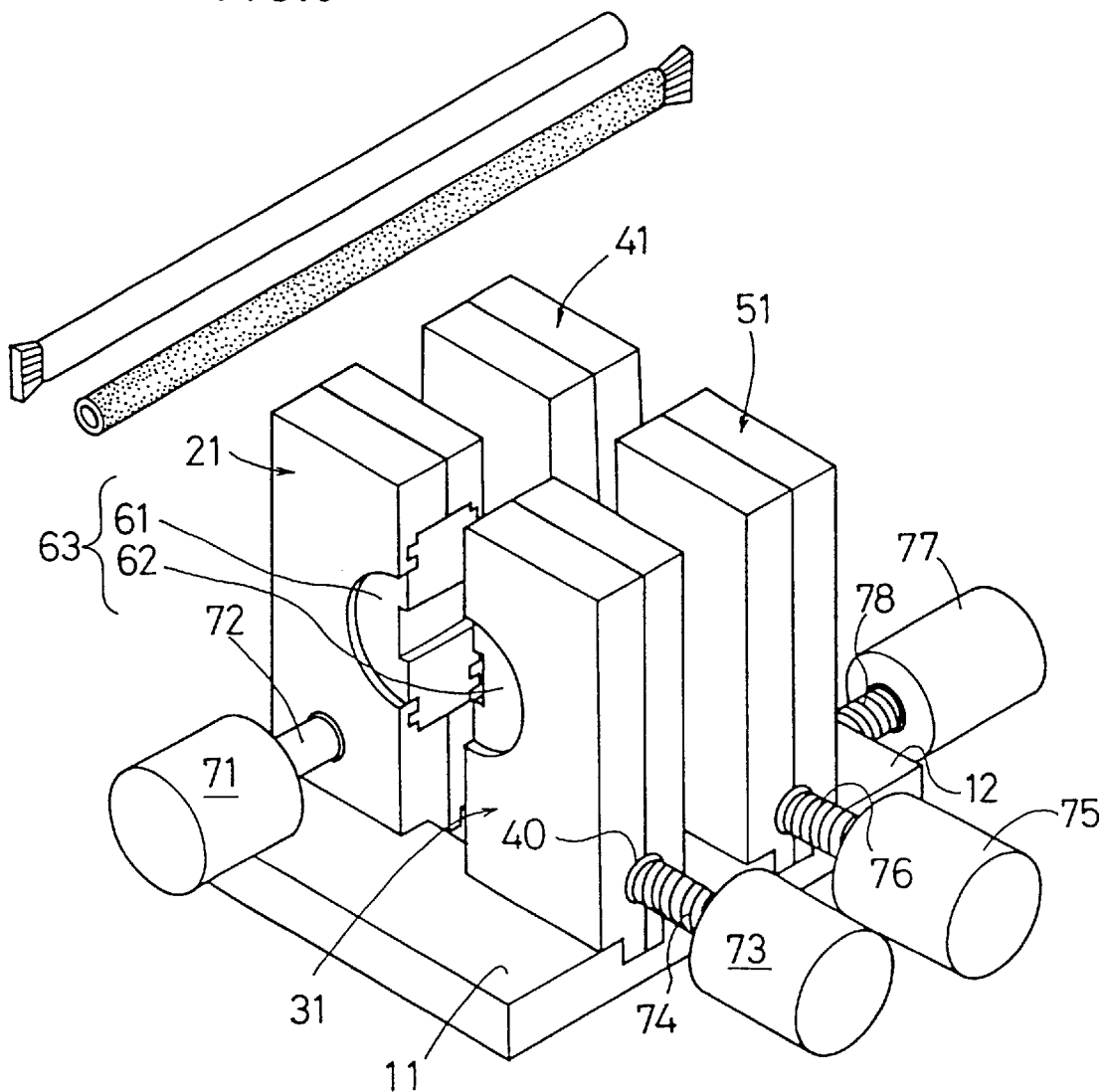
FIG. 6 is a perspective illustration showing driving means for driving the tube connecting apparatus.

The first tube holder 1 and the second tube holder 2 of the above-described constitution are mounted on the unillustrated body of the apparatus together with the driving means. Between the first tube holder 1 and the second tube holder 2, as described later, the cutting means is vertically movably mounted, and is engaged with a motor for giving the turning effort to the aforesaid drive gear 64, a motor for moving the movable clamps 31 and 51, and a motor for moving the second tube holder 2 towards the first tube holder 1 side. FIG. 6 is a perspective illustration showing driving means for driving the first tube holder 1 and the second tube holder 2.

In the driving means a motor 71 for transmitting rotation to the clamp rotor 63 is first connected to the drive gear 64 through a rotating axis 72. Also mounted are motors 73 and 75 for moving the movable clamps 31 and 51 towards the fixed clamps 21 and 41. The motors 73 and 75 have a screw portion on the rotating shafts thereof, and the screw portion is screwed into the screw holes 40 and 56 formed in the movable clamps 31 and 51. Furthermore, there is mounted a motor 77 for moving the second tube holder 2 for a very short distance towards the first tube holder 1 side. On the rotating axis 78 of the motor 77 is also formed a screw portion which is screwed into an unillustrated screw hole formed in the base 12.

The very short distance stated above for moving the second tube holder 2 is a distance for pressing to connect the melted ends of the tubes. The base 12 is mounted on an unillustrated rail and movably constituted as described above.

The motors 71, 73, 75 and 77 may be electric motors in general use, but it is preferable to use stepping motors which perform excellent positioning operation.

Figure 9:
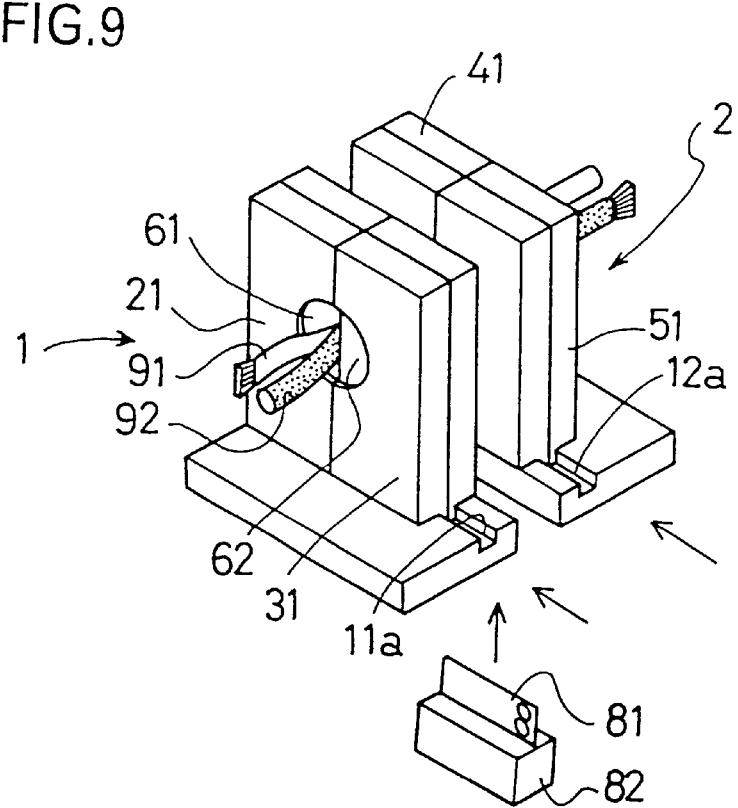
FIG. 9 is an external perspective illustration showing the first tube holder and the second tube holder with tubes set in the clamps.
Figure 10:
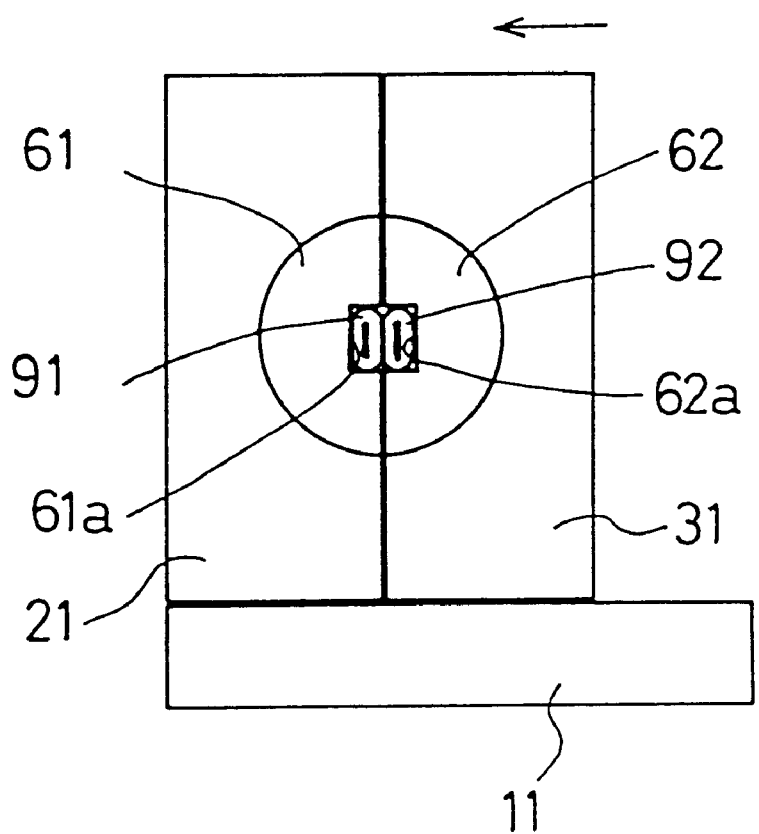
FIG. 10 is a view showing the section of the tubes set in the clamps.

Next, a cutting plate 81 is a self-heating type heating-cutting plate shown in FIG. 9. The cutting plate 81, though not shown in detail, is formed by folding a metal plate, for example a copper plate, into two, and forming a heating resistor of a desired pattern through an insulating layer on the inside surface thereof, and exposing terminals at both ends of the resistor out of an opening formed in one end of the metal plate. The cutting plate 81 is held on a cutting plate holding member 82 which vertically reciprocates. The cutting plate holding member 82 is made of a heat-resisting ceramic material or resin, and is driven by a cylinder 83 and others shown in FIG. 7. Furthermore, the cutting plate 81 is replaced every cutting operation with a new cutting plate 81 fed out of the cutting plate cassette by feeding means 84 shown in FIG. 7.

Figure 7:
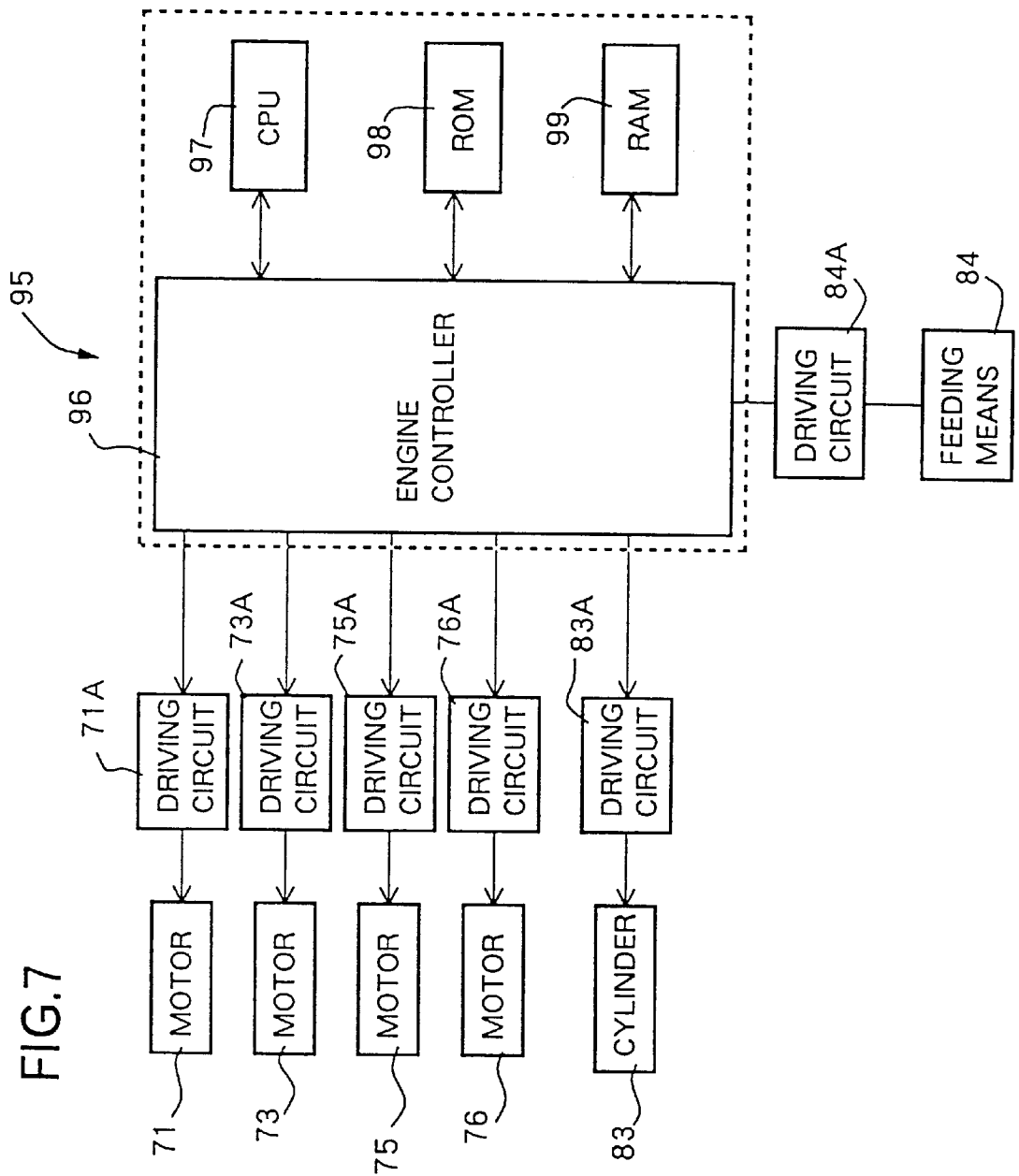
FIG. 7 is a block diagram showing a control unit.

Next, the control unit for controlling the tube connecting apparatus of the present embodiment will be explained. FIG. 7 is a block diagram showing the control unit. The control unit 95 has an engine controller 96, a CPU 97, a ROM 98, and a RAM 99, and carries out signal processing in accordance with a driving program stored in the ROM 98 while making use of the function of temporary storage of the RAM 99.

In this control unit 95 the engine controller 96 is connected to the motors 71, 73, 75, 76, the cylinder 83, and the feeding means 84 through the driving circuits 71A, 73A, 75A, 76A, 83A and 84A. A driving signal is outputted from the engine controller 96 to the driving circuits 71A, 73A, 75A, 76A, 83A and 84A, to thereby control the driving of the motor 71, 73, 75, 76, the cylinder 83, and the feeding means 84 as described later.

The tube connecting apparatus of the present embodiment constituted as described above is designed to cut two flexible tubes made of a flexible resin such as flexible polyvinyl chloride, and then to connect the cut ends of these tubes. For instance when a peritoneopathy patient needs a peritoneum dialysis, as heretofore described, the present apparatus is used. The function of the present apparatus, therefore, will be concretely explained by referring to FIGS. 8 to 13. The driving means including the motors 71, 73, 75 and 77 is not illustrated in the drawings.

Figure 8:
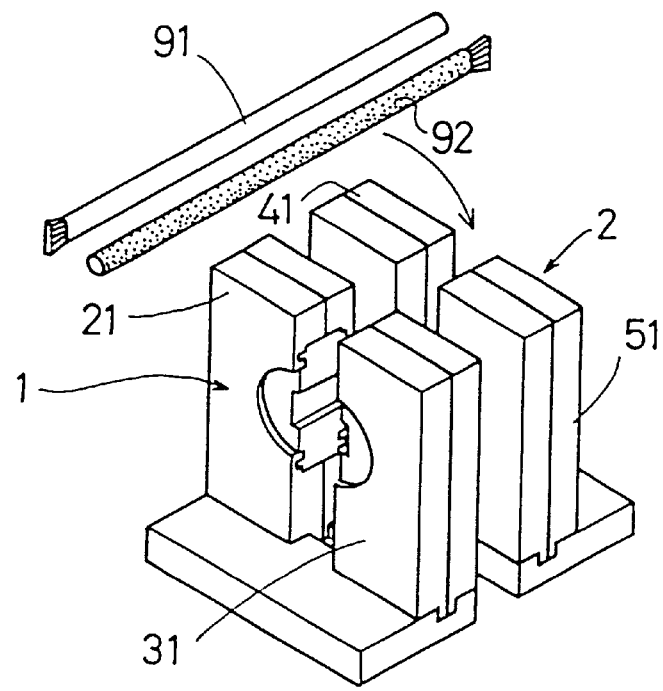
FIG. 8 is an external perspective illustration showing the first tube holder and the second tube holder prior to tube setting.

First, as shown in FIG. 8, the fixed clamps 21 and 41 and the movable clamps 31 and 51 of the first tube holder 1 and the second tube holder 2 are in separated positions. In this state, the user sets two tubes 91 and 92 in these clamps. To describe concretely, between the grasping portions 61b and 62b formed in the rotor pieces 61 and 62 in the first tube holder 1 and between the grasping portions 45 and 55 of the second tube holder 2 located at the same level as the first tube holder 1, tubes 91 and 92 are parallelly arranged.

After the setting of the tubes 91 and 92 on the apparatus, the switch provided on the unillustrated body of the apparatus is depressed to ON. In the present apparatus, the user performs only taking out this tube setting and tube removal after connection. Tube grasping and connecting operations are performed automatically by the control means 95.

First, when the motors 73 and 75 are started, the turning effort is transmitted from the motors 73 and 75 to the movable clamps 31 and 51 through the rotating axes 74 and 76. That is, the rotating axes 74 and 76 screwed in the screw holes 40 and 56 of the movable clamps 31 and 51 rotate to move the movable clamps 31 and 51 towards the fixed clamps 21 and 41. Then, when the movable clamps 31 and 51 have come into contact with the fixed clamps 21 and 41 as shown in FIG. 9, the motors 73 and 75 stop turning, and accordingly the movable clamps 31 and 51 also stop moving. At this time, the tubes 91 and 92 placed between the grasping portions 61b and 62b and the grasping portions 45 and 55 are squeezed to close, becoming flattened in cross section. Therefore, liquid leakage from the tubes 91 and 92 will be prevented at the grasping portions 61b and 62b and the grasping portions 45 and 55.

Figure 11:
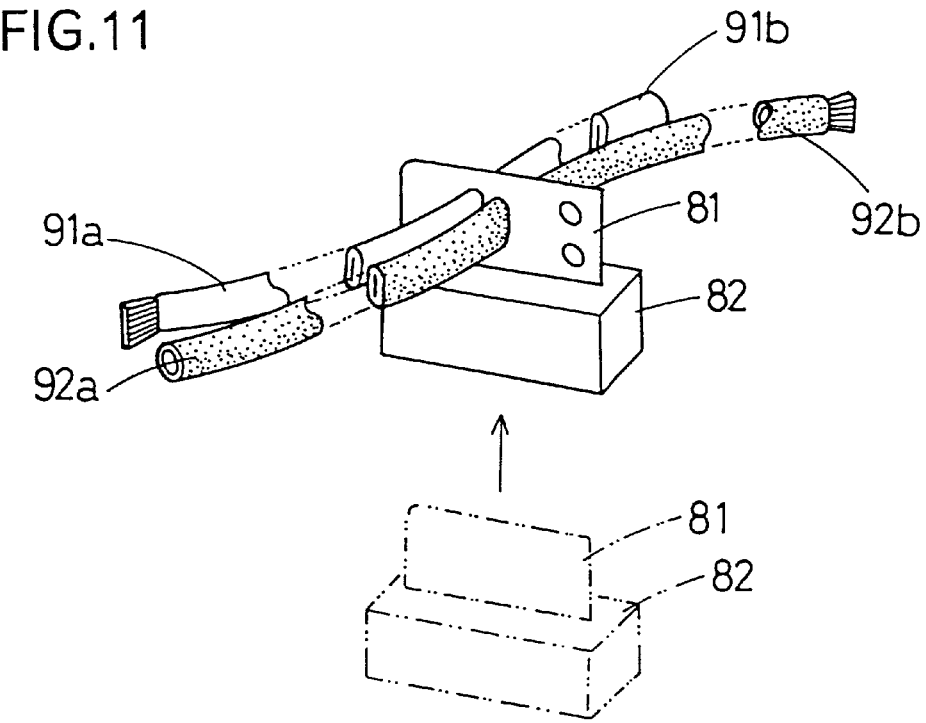
FIG. 11 is a perspective illustration showing the tubes at the time of cutting.

After the tubes 91 and 92 are squeezed to close by the grasping portions 61b and 62b and the grasping portions 45 and 55, the cutting plate 81 disposed between the first tube holder 1 and the second tube holder 2 is moved upwardly by the cylinder 83 towards the tubes 91 and 92. Then, as shown in FIG. 11, the cutting plate 81 cuts the tubes 91 and 92 vertically in the cutting position between the grasping portions 61b and 62b and the grasping portions 45 and 55. That is, when the electric voltage is applied to the cutting plate 81 newly mounted on the cutting plate holding member 82 attached by the feeding means 84, the heating temperature rises to 300 to 350° C. Then, the cutting plate 81 goes upwards to cross the tubes 91 and 92, thus melting to cut these tubes 91 and 92.

The cutting plate 81 will stop at a position shown in FIG. 11 where the tubes 91 and 92 have been cut. Subsequently the motor 71 is driven to turn the drive gear 64 by the rotating effort from the motor through the rotating axis 72. The rotation of the drive gear 64 is transmitted to the clamp rotor 63 which is in mesh with the drive gear 64. The motor 71 is driven until the clamp rotor 63 turns through 180 degrees.

Figure 12:
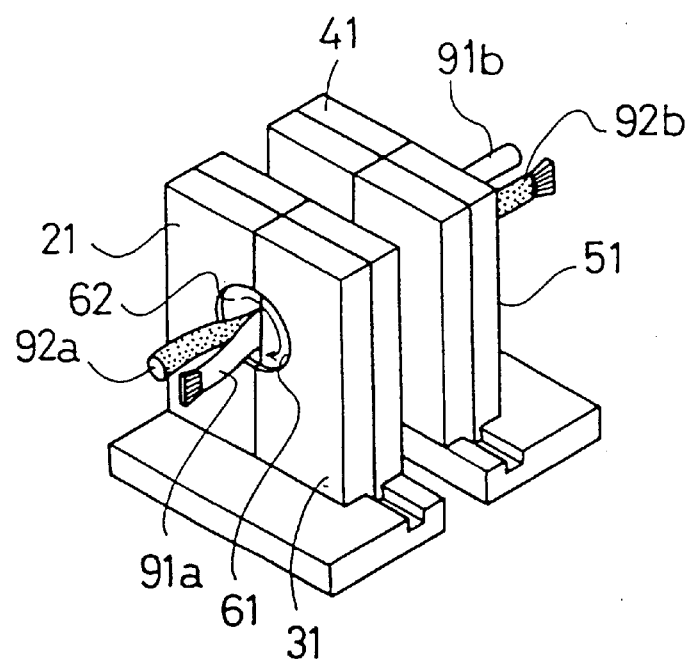
FIG. 12 is an external perspective illustration showing the first tube holder and the second tube holder with the clamp rotor turned.
Figure 13:
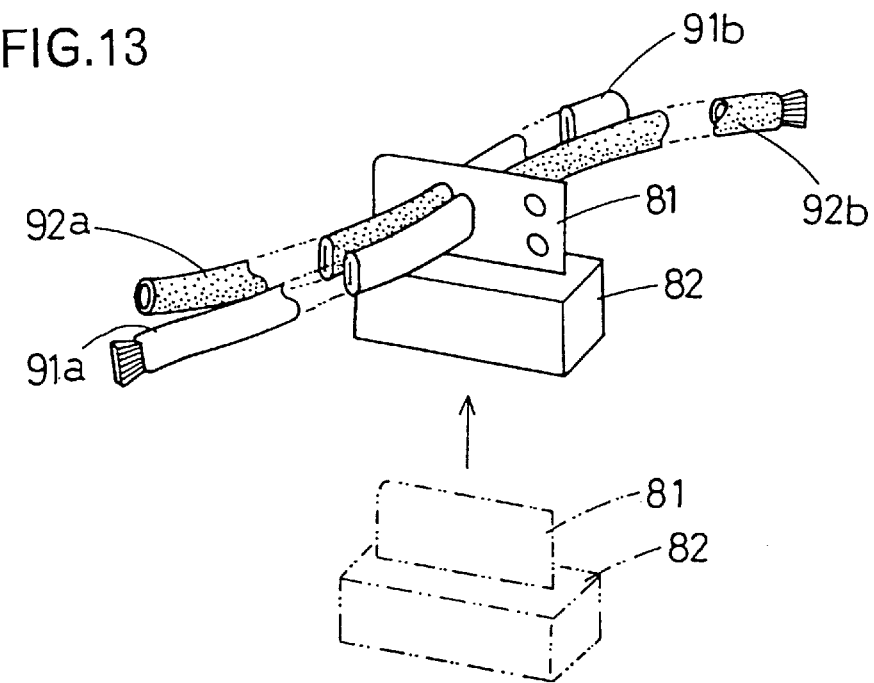
FIG. 13 is a perspective illustration showing the tubes after the clamp-rotor is turned.

Subsequently, as the clamp rotor 63 turns 180 degrees, the rotor pieces 61 and 62 are mutually translocated, within the fixed clamp 21 and the movable clamp 31, so that, as shown in FIG. 12, the cut ends of the tubes 91a and 92a grasped in the first tube holder 1 turn 180 degrees along the side surface of the cutting plate 81, thus changing positions. Therefore, as shown in FIG. 13, the cut end of the tube 91a will face the cut end of the tube 92b and the cut end of the tube 92a will face the cut end of the tube 91b respectively across the cutting plate 81. In this position, the clamp rotor 63 will be locked from easily turning by an unillustrated locking mechanism, for instance a toothed hook.

The cut ends of the tubes 91 and 92 are hot in a condition of melted or softened resin, and therefore are in contact in an airtight manner with the cutting plate 81. Therefore the cut ends of the tubes 91 and 92 turn along the side surface of the cutting plate 81 in this airtight condition, thus preventing the interior of the tubes 91 and 92 from being exposed to the atmosphere and maintaining the tubes in an aseptic condition.

Figure 14:
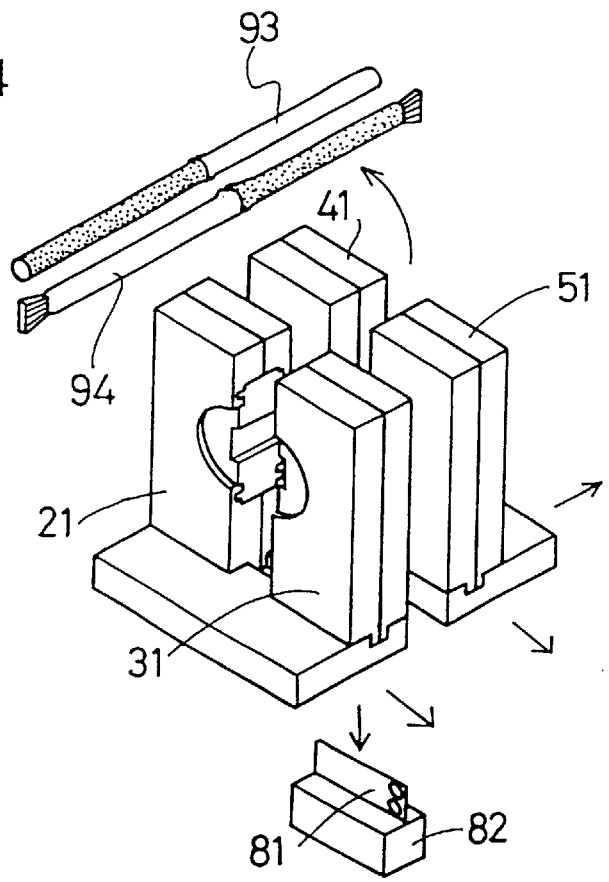
FIG. 14 is an external perspective illustration showing the first tube holder and the second tube holder after the tubes are taken out.

Then, upon the downward retreat of cutting plate 81, the second tube holder 2 is moved to the first tube holder 1. That is, when the motor 77 is driven, the output of the motor is transmitted to the base 12 through the rotating axis 78, thereby moving the base 12 for a very short distance towards the first tube holder 1 by the rotation of the rotating axis 78 which is screwed into the screw hole of the base 12. This is for moving the tubes by the same amount as the cutting thickness (the thickness of the cutting plate 81) and squeezing the tube ends. Thus the cut ends of the tubes 91b and 92b and the tubes 92a and 91a will be melted and connected, forming two tubes 93 and 94 alternately translocated as shown in FIG. 14.

Thereafter the motors 73 and 75 turn reversely, transmitting the rotational output to the movable clamps 31 and 51 through the rotating axes 74 and 76. That is, the rotating axes 74 and 76 screwed in the screw holes 40 and 56 of the movable clamps 31 and 51 rotate to move the movable clamps 31 and 51 backwards as shown in FIG. 14. At the same time, the motor 77 turns reversely to transmit the rotational output to the base 12 through the rotating axis 78. The base 12 also moves backwards.

The user then takes out the tubes 93 and 94 thus released, from between the fixed clamps 21 and 41 and the movable clamps 31 and 51 separated.

According to the tube connecting apparatus of the first embodiment described above, since it has become possible to realize the automatization of all operations including tube holding, cutting and connection, the tube connecting apparatus is easy to handle even to a physically disabled person. That is, because of the adoption of the clamp rotor 63 provided with the grasping portions 61b and 62b, the movable clamps 31 and 51 and the clamp rotor 63 can be operated independently, thus enabling automatization of a series of operations and accordingly reducing the time required for tube connection.

Also because the clamp rotor 63 in the fixed clamp 21 and the movable clamp 31 rotates, there is no disadvantage such as interference of the driving means with the tubes 91 and 92.

Furthermore, because the tubes 91 and 92 are parallelly arranged between the fixed clamps 21 and 41 and the movable clamps 31 and 51, such a disadvantage as the entanglement of the connected tubes at the time of removal has been obviated.

Next, the second embodiment of the present invention will be explained.

Figure 15:
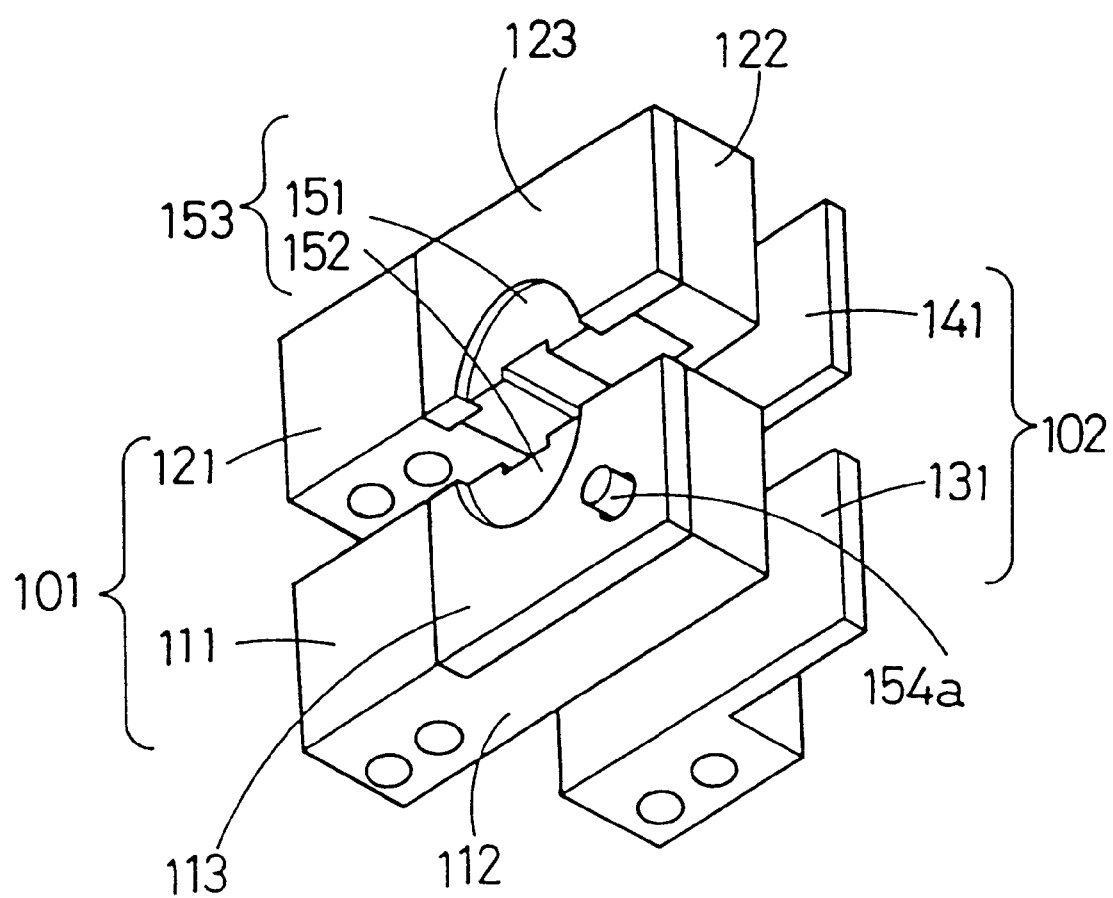
FIG. 15 is an external perspective illustration showing the clamp of the tube connecting apparatus of the second embodiment according to the present invention.

FIG. 15 is an external perspective illustration viewing from below the clamp section of the tube connecting apparatus of the present embodiment. The clamp section for grasping tubes comprises the first tube holder 101 and the second tube holder 102, which are engagedly mounted on the body of the apparatus. On the first tube holder 101 and the second tube holder 102, the movable clamps 121 and 141 which can be moved into contact with, and away from, the fixed clamps 111 and 131. That is, the fixed clamps 111 and 131 are fixedly mounted on the body of the apparatus, and in the meantime the movable clamps 121 and 141 are vertically slidably mounted to form the clamp section.

Figure 16:
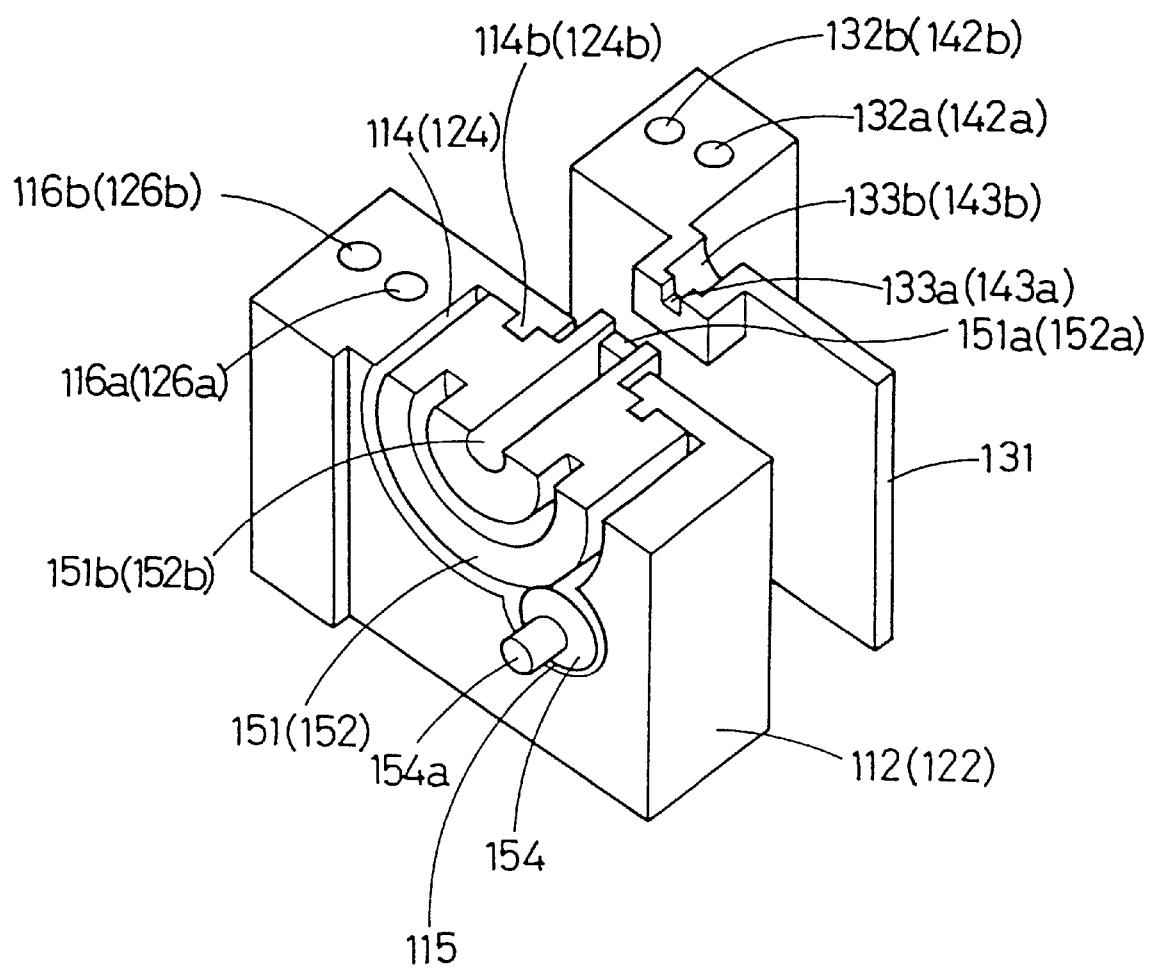
FIG. 16 is an external perspective illustration showing fixed clamps 111 and 131 of a first tube holder 101 and a second tube holder 102 of the second embodiment.
Figure 17:
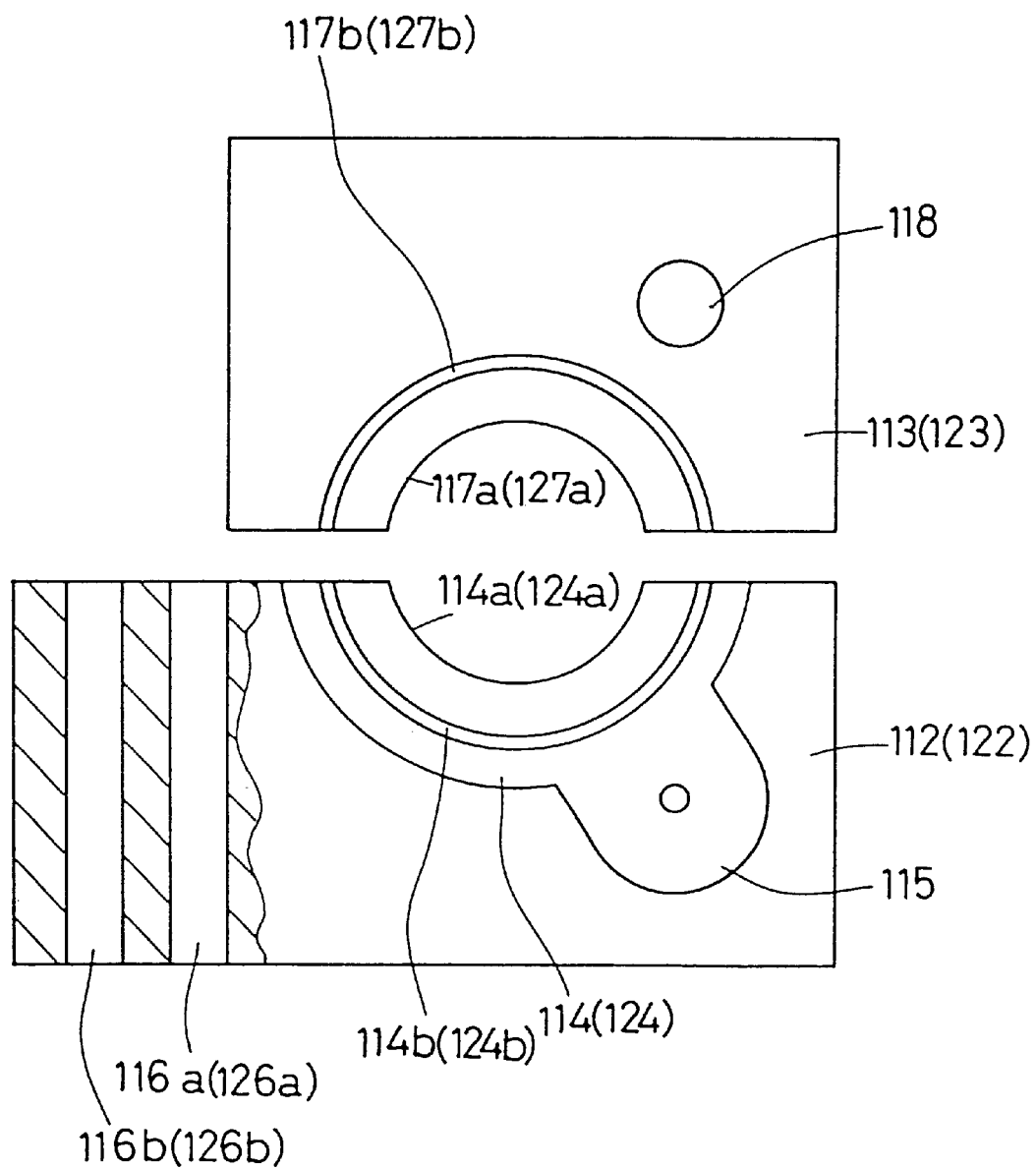
FIG. 17 is a view showing the interior of a fixed clamp 111 and a movable clamp 121 of the first tube holder 101 of the second embodiment.

The clamp section of the tube connecting apparatus has a rotating mechanism in the first tube holder 101; the second tube holder 102 is not provided with a rotating mechanism. Here, FIG. 16 is an external perspective illustration showing the fixed clamps 111 and 131 of the first tube holder 101 and the second tube holder 102. FIG. 17 shows the fixed clamp 111 of the first tube holder 101. The fixed clamps 111 and 131 and the movable clamps 121 and 141 are vertically symmetrical, and therefore only the fixed clamps 111 and 131 are shown. The constitution of the movable clamps 121 and 141 is indicated in parentheses.

First, therefore, the first tube holder 101 having the rotating mechanism will be explained. As seen from FIG. 15, both the fixed clamp 111 and the movable clamp 121 is formed by attaching covers 113 and 123 to the blocks 112 and 122 in which the rotor is mounted. Furthermore, as shown in FIG. 16, in the block 112 (122) is formed a rotor mounting section 114 (124) in which a semi-circular recess is provided. In this rotor mounting section 114 a clamp rotor 153 is mounted in either of a pair of semi-circular rotor pieces 151 and 152 constituting the holder.

As shown in FIG. 17, a semi-circular cutout 114a (124a) is formed in the central part of the rotor mounting section 114 (124). Also, in the rotor mounting section 114 (124) a peripheral rail 114b (124b) is formed. The peripheral rail 114b (124b) is a projecting rail formed in a semi-circular shape. The block 122 is provided (the block 122 is not provided) with the gear mounting section 115 formed continuing to the rotor mounting section 114. Furthermore, the blocks 112 and 122 are provided with guide holes 116a and 116b (126a and 126b) through which two guide shafts are vertically mounted.

In the meantime, in the cover 113 (123) are formed semi-circular cutout 117a (127a) and a semi-circular peripheral rail 117b (127b) correspondingly to the blocks 112 and 122. The cover 113 is provided (the cover 123 is not provided) with a through hole 118 through which a rotating axis 154a of a later-described drive gear 154 is mounted as shown in FIG. 15.

Figure 18:
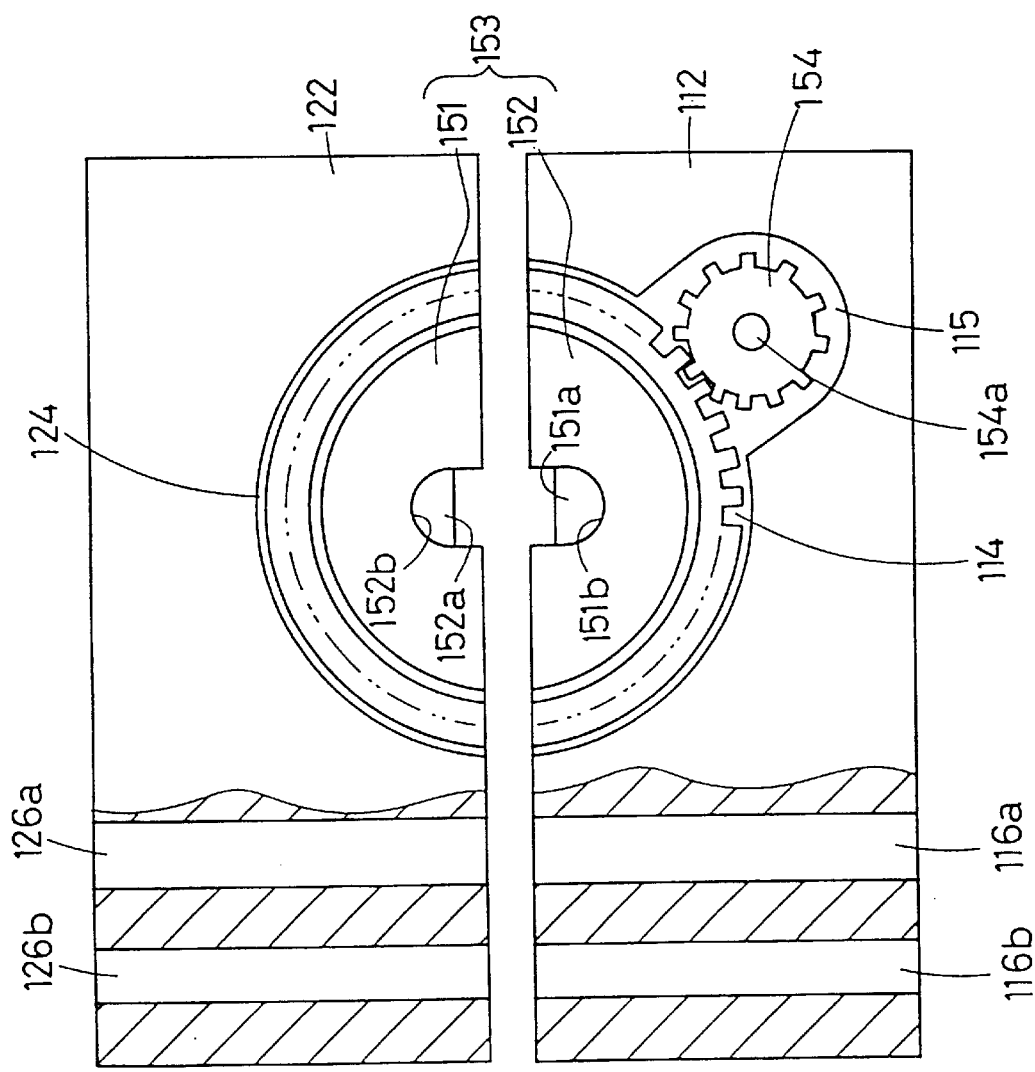
FIG. 18 is a view showing blocks 112 and 122 of the first tube holder 101 mounted with a clamp rotor of the second embodiment.

Next, FIG. 18 shows blocks 112 and 122 of the first tube holder 101 mounted with a clamp rotor 153. The clamp rotor 153 mounted in the blocks 112 and 122 consists of a pair of semi-circular rotor pieces 151 and 152, is provided with teeth formed on the periphery thereof, and is so constituted as to make one gear when both rotor pieces 151 and 152 come in contact with each other.

In the gear mounting section 115 there is rotatably mounted the drive gear 154 which is in mesh with the rotor pieces 151 and 152 and directly coupled with the rotating axis of the driving motor.

At the center of the clamp rotor 153, that is, at the center of the contact surfaces of the rotor pieces 151 and 152, U-grooves 151b and 152b are formed deep enough to allow the insertion of one tube as shown in FIG. 16; and formed at the end of the grooves are grasping portions 151a and 152a which protrude on the opposite side of the second tube holder 102 to squeeze and grasp the tubes. The grasping portions 151a and 152a are formed so high as to hold flattened ends of two tubes when the two tubes are set one on top of the other and squeezed. This is for closing the cut ends of the tubes in order to prevent fluid leakage from the tubes.

Next, in the second tube holder 102, as shown in FIG. 16, both clamps 131 (141) are provided with drilled guide holes 132a and 132b (142a and 142b) which are vertically guided along two guide shafts; and a grasping portion 133a (143a) is formed projecting to the first tube holder 101 side. A U-groove 133b (143b) similar to those formed in the rotor pieces 151 and 152 and deep enough to insert one tube therein is formed projecting to the first tube holder 101 side. At the end thereof a grasping portion 133a (143a) is formed.

Figure 22:
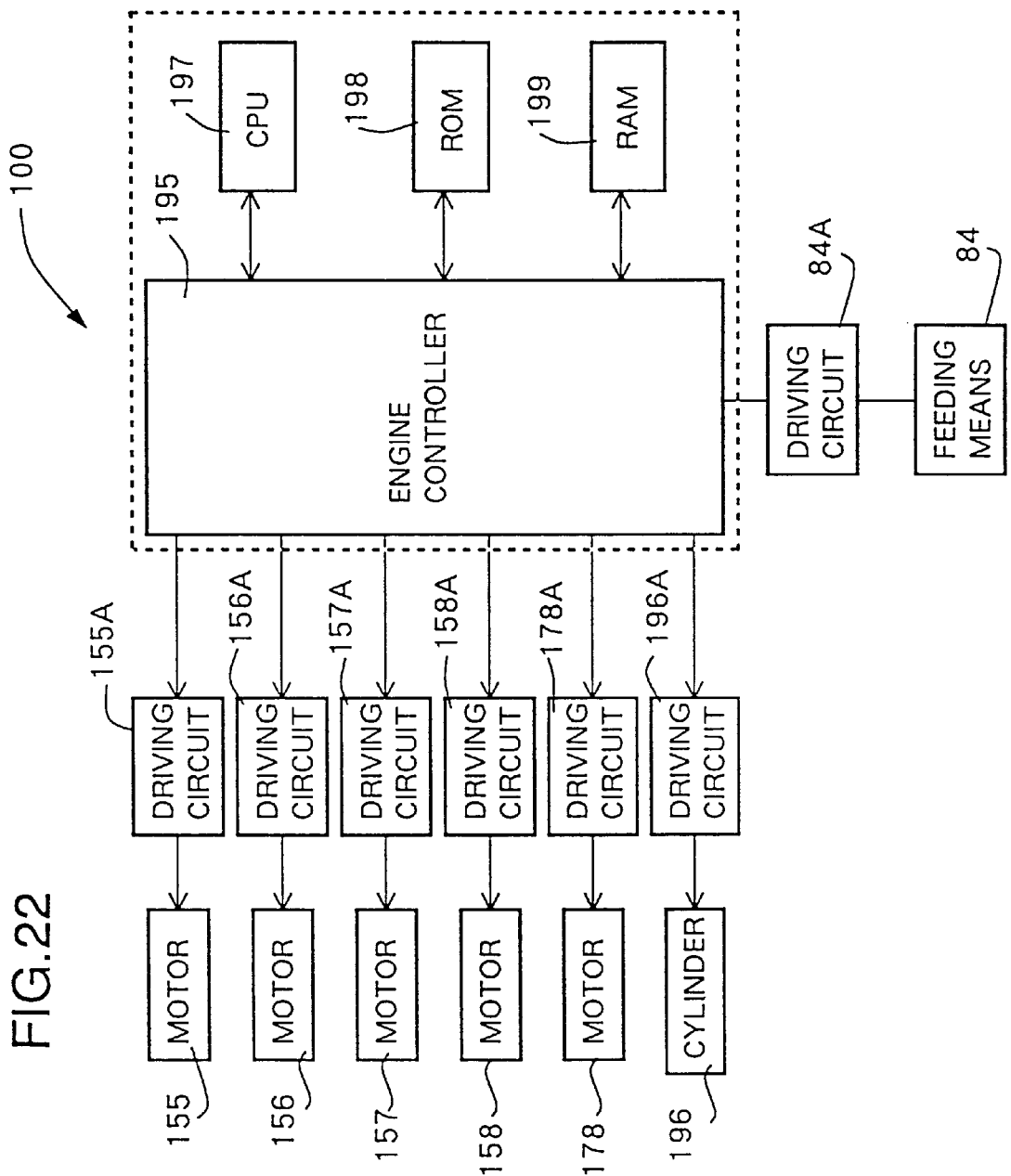
FIG. 22 is a block diagram showing the control unit of the tube connecting apparatus of the second embodiment.

Next, FIG. 22 is a block diagram showing the control unit of the tube connecting apparatus. Between the first tube holder 101 and the second tube holder 102 there is vertically movably disposed the cutting plate 105 which is tube cutting means as described later, and is coupled with a motor 155 for giving a turning effort to the aforementioned drive gear 154, motors 156 and 157 for moving the movable clamps 121 and 141, and a motor 158 for moving the second tube holder 102 towards the first tube holder 101.

To the driving means, first the motor 155 for transmitting rotation to the clamp rotor 153 is connected to the drive gear 154 through the rotating axis 154a. Furthermore, there are mounted motors 156 and 157 for moving the movable clamps 121 and 141 into contact with, and away from, the fixed clamps 111 and 131 respectively. To move the movable clamps 121 and 141 into contact with, and away from, the fixed clamps 111 and 131, it is conceivable to adopt such a constitution that an eccentric cam in contact with the movable clamps 121 and 141 is mounted on the rotating axes of the motors 156 and 157.

Furthermore, the motor 158 is mounted for moving the second tube holder 102 for a very short distance towards the first tube holder 101. In this case also, there may be mounted an eccentric cam on the rotating axis of the motor 158 to slide the second tube holder 102 for a very short distance towards the first tube holder 101 side. The above-mentioned very short distance for moving the second tube holder 102 is meant by a distance necessary for squeezing to connect the melted ends of tubes.

The motors 156, 157, 158 and 178 may be motors in general, but are preferably stepping motors which have an excellent positioning function.

In the meantime, tubes are carried by a support 171 to between the fixed clamps 111 and 131 and the movable clamps 121 and 141 thus disposed, particularly, one on top of the other in the holding position in the upper and lower U-grooves 151b and 152b where the grasping sections 151a, 152a, 133a and 143a are formed.

The support 171 is constituted such that the tubes 103 and 104 will be carried to the holding position from outside of the space of movement where the movable clamps 121 and 141 are vertically arranged. That is, this constitution is a part featuring the present invention, which has solved the aforesaid problems of conventional tube connecting apparatus. Hereafter, therefore, the support 171 will be explained in detail.

Figure 19:
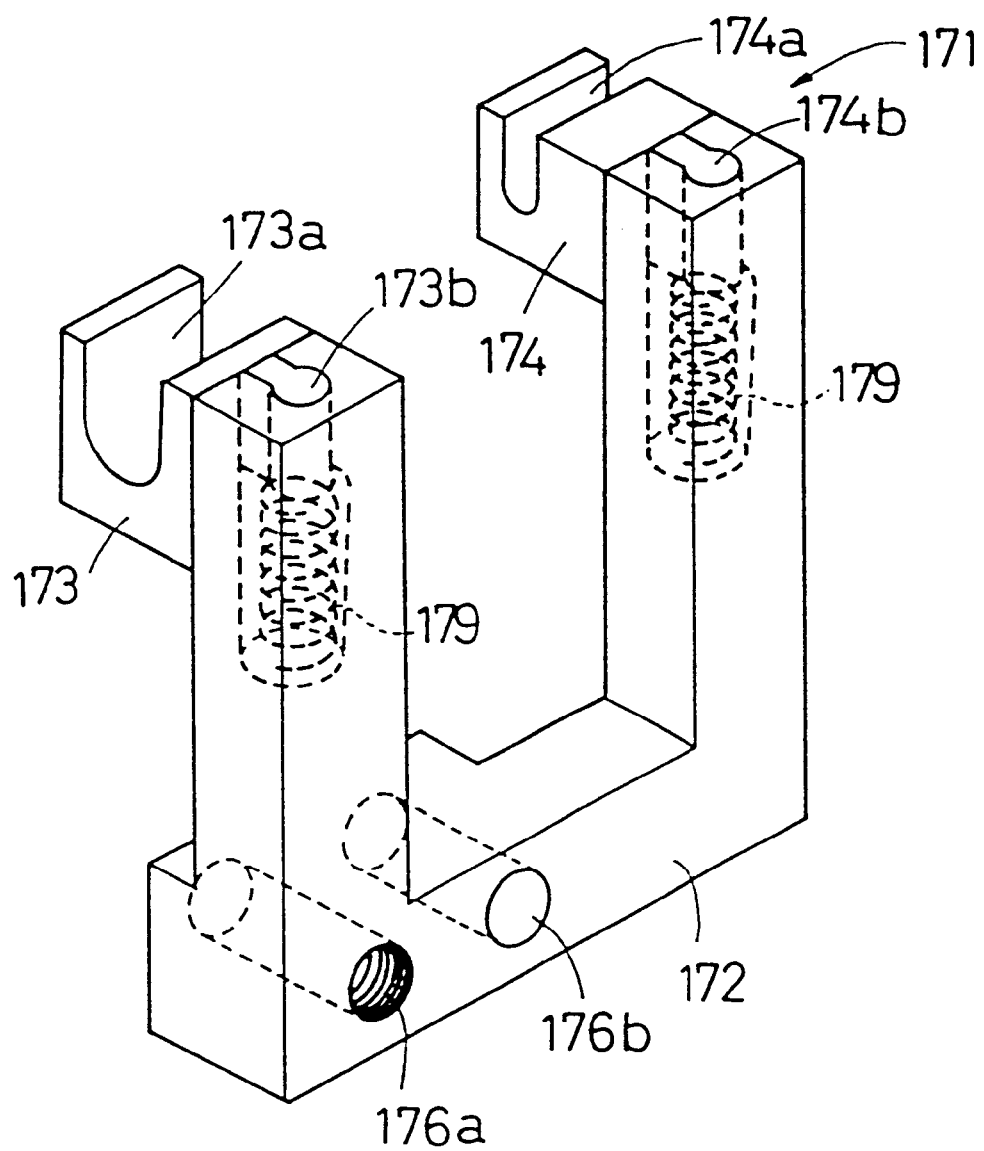
FIG. 19 is an exterior perspective illustration showing a support 171 of the tube connecting apparatus of the second embodiment.

FIG. 19 is an external perspective view showing the support 171. A body 172 of the support 171 is formed of a U-shaped square member, on both ends of which the holders 173 and 174 are engaged. The holders 173 and 174 are both formed such that the U-grooves 173a and 174a are aligned in the same direction.

The width of the U-groove 174a of the holder 174 present on the second tube holder 102 side is nearly the same as the outside diameter of the tubes 103 and 104, while the width of the U-groove 173a of the holder 173 on the first tube holder 101 side is formed nearly twice as large as the outside diameter of the tubes 103 and 104. This is because the tubes 103 and 104 are firmly supported by the holder 174, and for the purpose of preventing the tubes 103 and 104 turned by the clamp rotor 153 in the holder 173 from being twisted in the grooves.

On the holders 173 and 174 are formed projections 173*b* and 174*b* which fit in rail grooves formed in the body 172 and supported in the illustrated state by springs 179, 179 inserted in the body 172; and furthermore a sliding mechanism is provided to slide the projections up and down.

Figure 20:
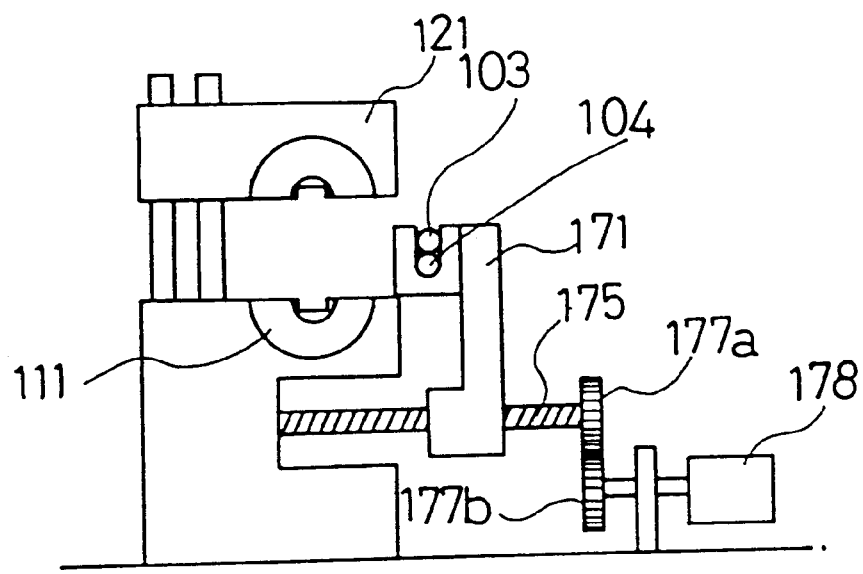
FIG. 20 is a schematic view showing a feed mechanism of a support of the tube connecting apparatus of the second embodiment.
Figure 21:
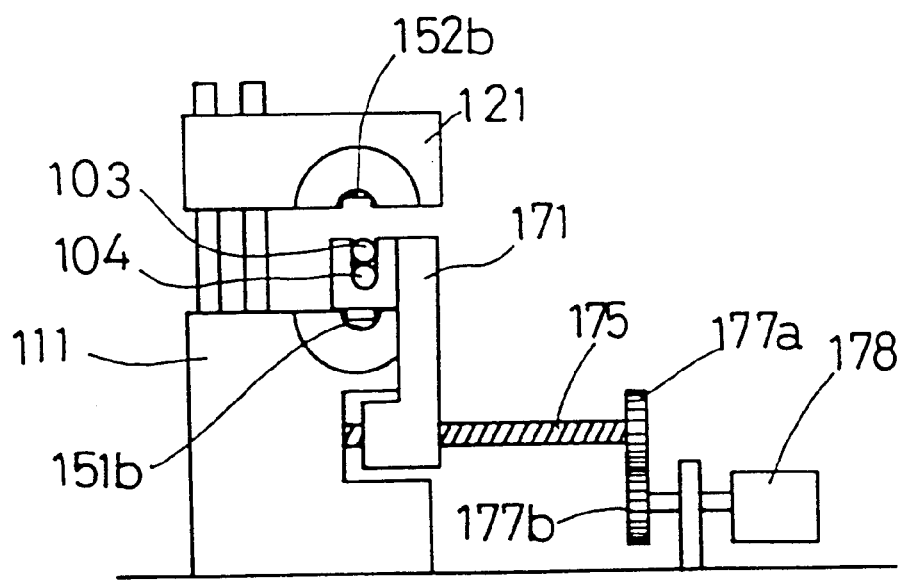
FIG. 21 is a schematic view showing the feed mechanism of the support of the tube connecting apparatus of the second embodiment.

FIGS. 20 and 21 are side views of the feed mechanism of the support 171. FIGS. 20 and 21 show the operating condition, which will be described later.

In the support 171 a feed screw 175 which is rotatably engaged with an internal screw 176*a* (FIG. 19) formed in the body 172. Then, the gear 177*a* secured on the feed screw 175 and a gear 177*b* secured on the output shaft of the motor 178 are engaged to transmit the motor power.

In the meantime, a guide hole 176*b* is provided (FIG. 19) in parallel with the internal screw 176*a* in the body 172 of the support 171, and the guide shaft provided in the body of the apparatus is inserted through, thus functioning to stop rotation.

In the meantime, the cutting plate 105 for cutting tubes is a self-heating type heating-cutting plate. The cutting plate 105 is made by folding a metal plate, such as a copper plate, into two, forming a heating resistor of a desired pattern through an insulating layer on the inner surface, and exposing terminals on both ends of the resistor out of an opening formed in one end of the metal plate.

The cutting plate 105 is held by the cutting plate holding member which reciprocates up and down. The cutting plate holding member is produced of a heat-resisting ceramic or resin material, and connected to the cylinder 196 (FIG. 22) for positioning. Also, the cutting plate 105 is replaced every operation with a new cutting plate 105 which is fed out one by one from the cutting plate cassette.

Next, a control unit for controlling the tube connecting apparatus of the second embodiment will be explained. FIG. 22 is a block diagram showing the control part of the tube connecting apparatus. A control unit 100 has an engine controller 195, a CPU 197, a ROM 198, and a RAM 199, and carries out signal processing in accordance with a driving program stored in the ROM 198 while making use of the function of temporary storage of the RAM 199.

In this control unit 100 the engine controller 195 is connected to the motors 155, 156, 157, 158 and 178, through the driving circuits 155A, 156A, 157A, 158A and 178A. A driving signal is outputted from the engine controller 195 to the driving circuits 155A, 156A, 157A, 158A and 178A, to thereby control the driving of the later-described motors 155, 156, 157, 158 and 178. The cylinder 196 also is connected to the engine controller 195 through the driving circuit 196A.

Therefore, the tube connecting apparatus of the second embodiment performs cutting and connection of tubes by the following operation.

The user first sets tubes 103 and 104 one on top of the other in the support 171 as shown in FIG. 20. At this time, the holders 73 and 174 in which the tubes 103 and 104 are set are disposed outside of the grasping area in which the movable clamps 121 and 141 move up and down, and therefore the user is required only to hold, by both hands, the tubes 103 and 104 in such a manner that the length of the portion of the tubes thus held is longer than the distance of the holders 173 and 174, and then to slip the tubes down into the U-grooves 173*a* and 174*a*. Subsequently to the insertion of the tubes 103 and 104, the switch is depressed to accomplish the following operation of the tube connecting apparatus. With the operating switch depressed to ON, the tube connecting apparatus is controlled as described below in accordance with a preset program.

First, the support 171 supporting the tubes 103 and 104 is moved to the holding position in which the tubes 103 and 104 will be clamped by the fixed clamps 111 and 131 and the movable clamps 121 and 141. A motor 178 starts to transmit its turning effort to a feed screw 175 through gears 177*a* and 177*b*. As the feed screw 175 rotates, there takes place a thrust at the support 171 being locked from rotation, thus moving the tubes 103 and 104 leftwards in FIG. 20. From the motor 178 a specific amount of rotation is imparted and the tubes 103 and 104 being fed on the support 171 are carried as far as the holding position including the upper and lower U-grooves 151*b* and 152*b* (133*b* and 143*b*) in which the tubes will be positioned one on top of the other as shown in FIG. 21.

Subsequently to the positioning of the tubes 103 and 104, first the motors 156 and 157 start to transmit their turning effort to the movable clamps 121 and 141 through for instance the rotation of the eccentric camp as described above. Thus the movable clamps 121 and 141 in contact with the eccentric cam move toward the fixed clamps 121 and 141 side along the cam face of the eccentric cam. When the movable clamps 121 and 141 come into contact with the fixed clamps 111 and 131, the motors 156 and 157 stop turning to stop the movement of the movable clamps 121 and 141. At this time, the tubes 103 and 104 set between the grasping portions 151*a* and 152*a* and the grasping portions 133*a* and 143*a* are squeezed flat to close, thereby preventing liquid leakage when the tubes 103 and 104 are cut at the grasping portions 151*a* and 152*a* and the grasping portions 133*a* and 143*a*.

The tubes 103 and 104 thus squeezed by the grasping portions 151*a* and 152*a* and the grasping portions 133*a* and 143*a* and held in the U-grooves 151*b*, 152*b*, 133*b* and 143*b* receive a load in one direction from the movable clamps 121 and 141 to the fixed clamps 111 and 131 side. The lower tube 104 is set on the tube 103 to receive an indirect load, while the tube 103 receives a local load from the grasping portions 152*a* and 143*a*.

Therefore, variations will occur in the load distribution of the tubes 103 and 104, and also in the sectional form. Particularly the amount of deformation of the tube 103 which directly receives the load from the grasping portions 143*a* and 152*a* increases great, resulting in a different sectional form from the tube 104.

The above-described disadvantage, however, has been obviated by providing the holders 173 and 174 with the sliding mechanism.

Figure 23:
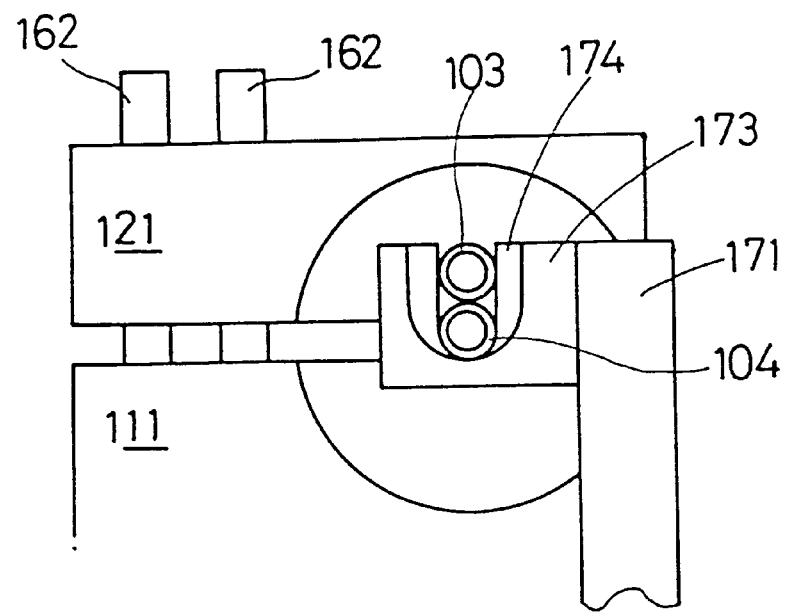
FIG. 23 is a side view showing a clamp of the tube connecting apparatus of the second embodiment.
Figure 24:
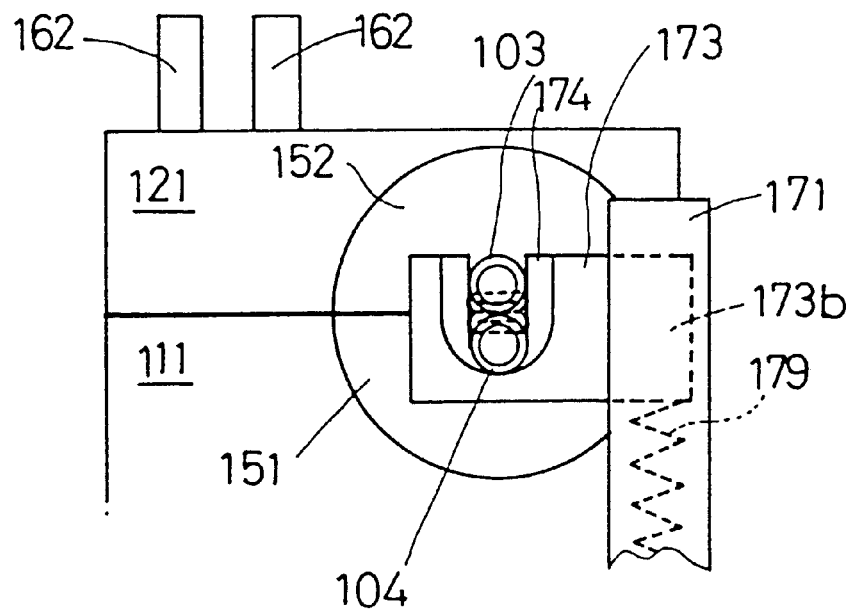
FIG. 24 is a side view showing the clamp of the tube connecting apparatus of the second embodiment.

First, of the tubes 103 and 104 positioned in the holding position by the support 171, the tube 104 is at a higher level than the upper surface of the fixed clamp 111 as shown in FIG. 23. Then, when the movable clamps 121 and 141 have gone down, the tubes 103 and 104, being clamped, are also moved down, and therefore the holders 173 and 174 are loaded through the descending tubes 103 and 104. Therefore, the holders 173 and 174, receiving load from the tubes 103 and 104, slide downwards against the force of the springs 179 as shown in FIG. 24.

As the holders 173 and 174 go downwards, the tubes 103 and 104 also descend, lowering the entire contact surface of the tubes 103 and 104 to the level at which the tubes 103 and 104 are grasped (indicated by a dot line in FIG. 24) by the grasping portions 133a and 143a and the grasping portions 151a and 152a. Thus the load being applied to the tubes 103 and 104 is balanced to uniformly compress the tubes flat.

Figure 25:
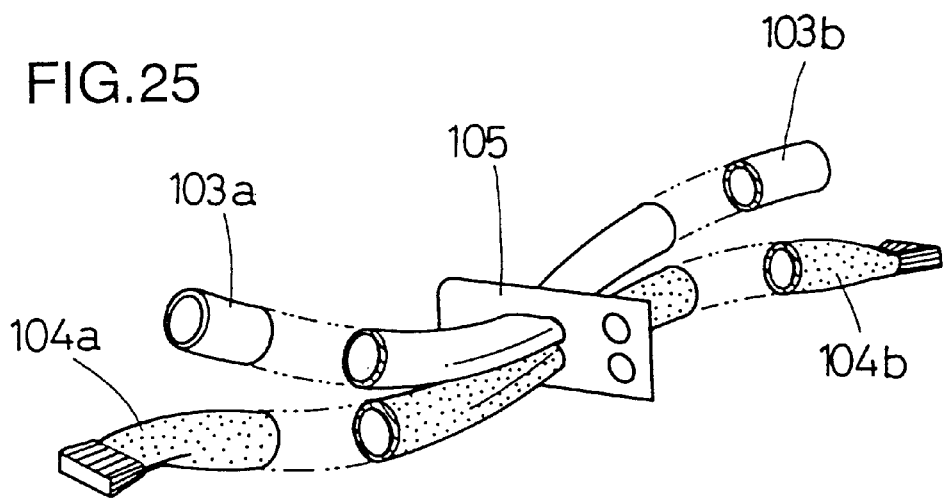
FIG. 25 is a schematic view showing the state of cut tubes.

After the tubes 103 and 104 are compressed to close by the grasping portions 133a and 143a and the grasping portions 151a and 152a, the cutting plate 105 disposed between the first tube holder 101 and the second tube holder 102 is moved upwards by the cylinder 196 towards the tubes 103 and 104. Then, as shown in FIG. 25, the cutting plate 105 vertically cuts the tubes 103 and 104 between the grasping portions 133a and 143a and the grasping portions 151a and 152a. That is, the cutting plate 105 newly mounted on the cutting plate holding member by the feeding means, when applied with the electric voltage, rises in temperature to 300 to 350° C., thereby melting to cut the tubes 103 and 104 when rising across the tubes 103 and 104.

The cutting plate 105 then stops at the position shown in FIG. 25 after cutting the tubes 103 and 104, and subsequently the motor 155 is driven to rotate the drive gear 154 by the turning effort through the rotating axis 154a. The rotation of the drive gear 154 is transmitted to the clamp rotor 153 which is in mesh with the drive gear 154. The motor 155 turns until the clamp rotor 153 turns through 180 degrees.

Figure 26:
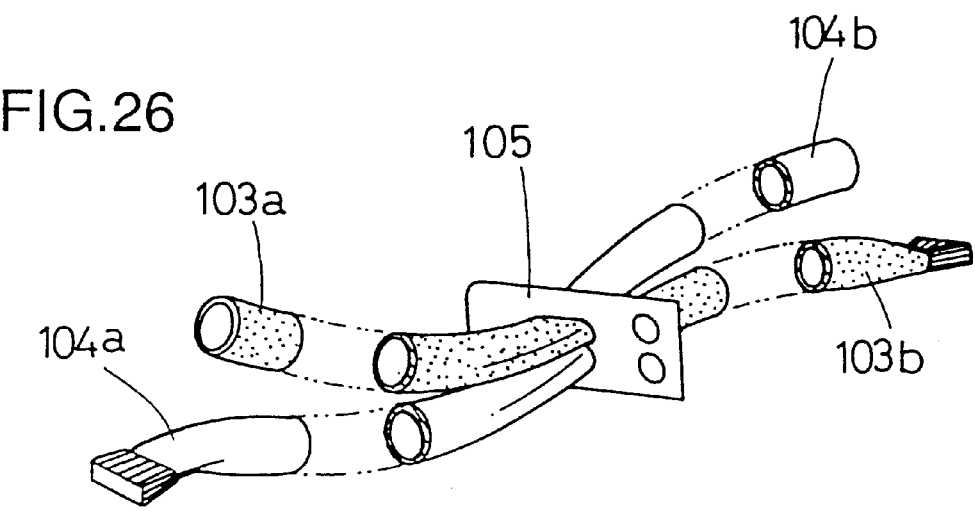
FIG. 26 is a schematic view showing the state of the tubes with the clamp rotor 153 rotated after tube cutting.
Figure 27:
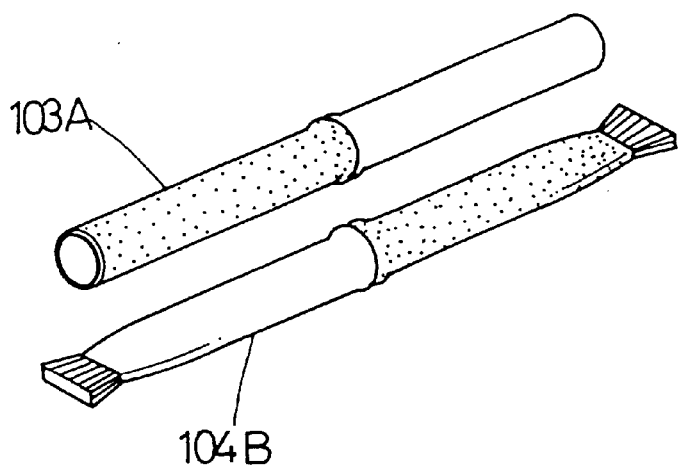
FIG. 27 is a view showing the tubes after connection.
Figure 28:
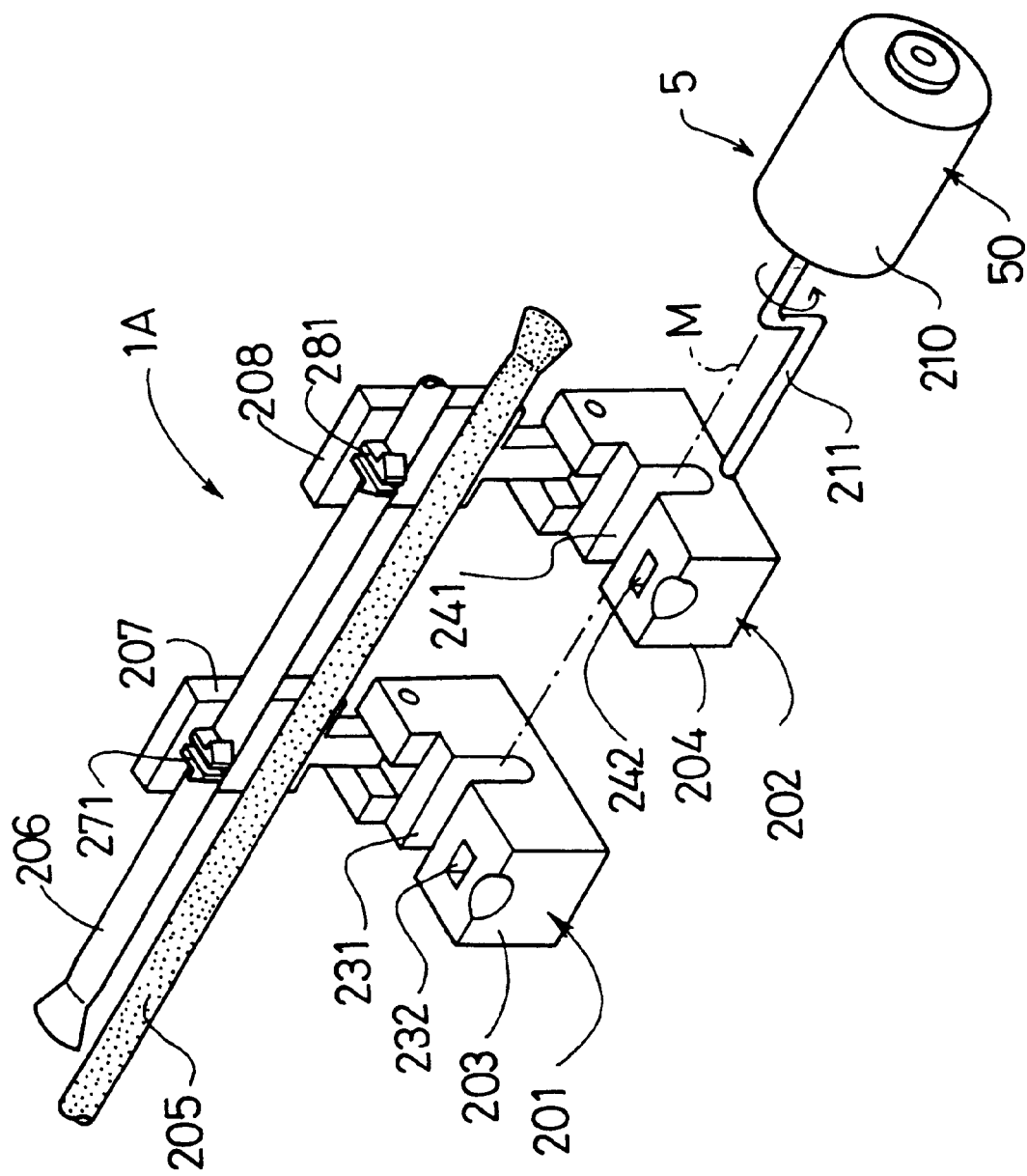
FIG. 28 is a perspective illustration showing a holder of a conventional tube connecting apparatus.

Then, as the clamp rotor 153 turns through 180 degrees, the rotor pieces 151 and 152 change positions in relation to the fixed clamp 111 and the movable clamp 121; and as shown in FIG. 26, the cut ends of the cut tubes 103a and 104a grasped on the first tube holder 101 turn 180 degrees along the side surface of the cutting plate 105, thus changing positions with each other. Accordingly, the cut portions, namely the cut ends of the tube 103a and the tube 104b and the cut ends of the tube 104a and the tube 103b, face each other. In this position, the clamp rotor 153 is locked by a locking mechanism such as a toothed hook in order not to rotate easily.

Since the holder 173 has a widely formed U-groove 173a, the tubes 103a and 104a held by the clamp rotor 153 rotate without being twisted.

The cut ends of the tubes 103 and 104 are hot with melted and softened resin, being in airtight contact with the cutting plate 105. Therefore the cut ends of the tubes 103 and 104, when rotating, rotate along the side surface of the cutting plate 105 while in airtight contact with the cutting plate 105. The interior of the tubes 103 and 104 can be kept aseptic without exposure to the atmosphere.

Next, the cutting plate 105 is moved back downwards by a cylinder 196 and at the same time the second tube holder 102 is moved to the first tube holder 101. That is, the motor 158 is driven to move the second tube holder 102 by an eccentric cam for a very short distance towards the first tube holder 101. This is for pressing to connect tubes by moving the second tube holder 102 for a cutting width (thickness of the cutting plate 105). The tubes 103b and 104b and the tubes 104a and 103a are melted and connected to each other at the cut ends, thus forming two tubes 103A and 104A which have been mutually translocated as shown in FIG. 13.

Thereafter the motors 156 and 157 turn further to withdraw the movable clamps 121 and 141. At the same time the motor 158 also turns further to withdraw the second tube holder 102.

Then, when the movable clamps 121 and 141 move away from the fixed clamps 111 and 131, the motor 178 turns reversely, thus turning the feed screw 175 to move the support 171 backwards. Therefore the support 171 holding the connected tubes 103A and 104B shown in FIG. 20 is moved back to the initial position shown in FIG. 6, where the user takes out the tubes 103A and 104B.

The tube connecting apparatus of the second embodiment has heretofore been explained. According to the present apparatus, the user is required only to insert the tubes 103 and 104 into the holders 173 and 174 of the support 171. It, therefore, becomes unnecessary to move the tubes 103 and 104 to between the fixed clamps 111 and 131 and the movable clamps 121 and 141 and to position the tubes in the holding portion, allowing easier handling of tube mounting.

Particularly, the holders 173 and 174 of the support 171, being disposed outside of the first tube holder 101 and the second tube holder 102, can be inserted very easily without interference when the tubes 103 and 104 are inserted.

In the holders 173 and 174 are formed U-grooves 173a and 174a, into which the tubes 103 and 104 can be just slipped down. The user, therefore, needs no special effort, and can handle the apparatus with ease.

Also, as previously stated, the holders 173 and 174 supporting the tubes 103 and 104 receive a reaction force of the tubes with respect to the body 172, or slide with the operating power of the clamp, thereby balancing the load applied to the tubes 103 and 104 at the time of grasping, flattening the tubes 103 and 104 to a uniform sectional form of their cut ends, and accordingly enabling mutual translocation and proper connection of the tubes.

One embodiment of the tube connecting apparatus according to the present invention has heretofore been explained. It should be noticed that the present invention is not limited the aforementioned embodiment and various modifications are possible within the scope of the invention.

For example in the above-described embodiment a motor is used in driving means, but a solenoid and a cylinder may be used in place of the motor.

Also, for example in the above-described embodiment, the clamp rotor 63 is mounted only in the first tube holder 1, but may be mounted also in the second tube holder 2 and mutually rotated.

Furthermore, for example in the above-described embodiment, two tubes are connected. The number of tubes to be connected, however, may be increased to three or more.

For example in the above-described embodiment, the movable clamps 31 and 51 are designed to contact the fixed clamps 21 and 41, but both the movable and fixed clamps may be movable.

In the above embodiment, the rotating power of the motor 178 is transmitted through the feed screw 175 to the support 171. An eccentric cam may be used instead for the feed screw.

According to the present invention, therefore, each of the first tube holder and the second tube holder is provided with a pair of clamps having a holding portion for holding a plurality of tubes. The pair of clamps can be moved into contact with, and away from, each other to grasp the tubes. The holding portion of one or both of the first tube holder and the second tube holder is rotatably disposed in the circumferential direction of the tubes thus grasped, and is provided with grasping means for moving into contact with, and away from, the pair of clamps of the first tube holder and the second tube holder, and rotating means for rotating one or both of the holding portions of the first tube holder and the second tube holder. It, therefore, has become possible to provide a tube connecting apparatus which the user can easily handle with reduced load and without interference between the driving means and the tubes.

Furthermore, according to the present invention, the holding portion for grasping the tubes comprises a pair of semi-circular clamp rotors rotatably mounted in a common circumferential grooves provided in a pair of clamps, and there is formed a cutout groove in the central part of the pair of clamp rotors in contact with each other. It is, therefore, unnecessary to take the provision of a space for rotation into account, and it has become possible to provide the tube connecting apparatus presenting no interference with other members.

Furthermore, according to the present invention, teeth are formed on the circumference of the clamp rotor which is the holding portion and are engaged with the drive gear in the clamp coupled with a motor which is rotating means; it, therefore, is possible to provide a tube connecting apparatus in which the driving means will not interfere with tubes.

Furthermore, according to the present invention, one of the pair of clamps is secured on a rail, while the other clamp is mounted movable on the rail by the grasping means. It is, therefore, has become possible to provide a tube connecting apparatus capable of reliably grasping tubes by moving on the rail.

Furthermore, according to the present invention, a preferable device can be selected from among motor, solenoid, and cylinder for the grasping means, thereby enabling to realize proper operation and cost reduction of the tube connecting apparatus.

Furthermore, according to the present invention, when the switch is operated, the control means drives the grasping means to move a pair of clamps of the first tube holder and the second tube holder, and after the clamps have come into contact with each other, the moving means is driven to move the cutting means to heat and melt the tubes. Subsequently, after the tube is cut by cutting means, the rotating means is driven to rotate the holding portion grasping the tubes; and after the rotation of the rotating means, the adjusting means is driven simultaneously with the withdrawal of the cutting means, to thereby move the first tube holder and the second tube holder closer to each other. And then a pair of clamps of the first tube holder and the second tube holder which are in contact with each other are away from by the grasping means. The user, therefore, can easily handle the apparatus with less burden. Also it is possible to provide a tube connecting apparatus in which no interference occurs between the driving means and the tubes.

According to the present invention, one or both of the holding portions of the first tube holder and the second tube holder are separated into rotatable members which have a rotation symmetry in relation to a center of a rotating axis. The tubes, after being cut by the cutting means, are turned for mutual translocation and connection. For tube positioning, there is provided supporting means which supports at least two tubes one over the other in the direction of movement of the holding portions and moves the tubes from outside of the grasping area of the holding portions to inside of said grasping area. Thus it has become possible to provide a tube connecting apparatus which facilitates tube mounting.

Furthermore, according to the present invention U-grooves are provided as a support of the supporting means, and therefore it has become possible to provide a tube connecting apparatus which enables the user to easily mount tubes only by slipping the tubes down into the grooves.

Furthermore, according to the present invention, the first tube holder and the second tube holder are disposed between the supports of the supporting means; the width of the U-groove of one support is nearly the same as the outside diameter of the tube, while the width of the U-groove of the other support is twice as large as the outside diameter of the tube. It, therefore, has become possible to provide a tube connecting apparatus which reliably holds the tubes in position on one side while allowing smooth rotation of the tubes on the other side without distortion and excessive force application.

Furthermore, according to the present invention, it has become possible to provide a tube connecting apparatus in which a sliding mechanism which changes positions when the support of the supporting means has receiving a load; and therefore uneven load on the upper and lower tubes can be balanced, thereby ensuring uniformly compressing tube ends into a flat form.

Furthermore, according to the present invention, it has become possible to provide a tube connecting apparatus which facilitates tube mounting. That is, transporting means for moving the supporting means determines the position of the support between two points of the tube mounting position outside of the grasping area of the holding portions and the holding position located within the grasping area; and therefore the user is required only to mount the tubes in the supports.

Furthermore, according to the present invention, it has become possible to provide a tube connecting apparatus in which since a motor, a solenoid, or a cylinder is selected as the transporting means, the most suitable driving source can be adopted with assembly with other mechanisms and cost taken into account.

What is claimed is:

1. A tube connecting apparatus comprising: a first tube holder and a second tube holder for receiving a plurality of flexible tubes, and cutting means for heating and melting said tubes thus received by said first tube holder and said second tube holder to cut said tubes between said first tube holder and said second tube holder, each of said first tube holder and said second tube holder having a holding portion for holding said tubes, the holding portion of at least one of said holders including a pair of semicircular separable pieces having a rotation symmetry in relation to a rotation axis, and said separable pieces having tube grasping recesses centered on the rotation axis.

2. A tube connecting apparatus according to claim 1, wherein, said holding portion includes peripheral gear teeth.

3. A tube connecting apparatus according to claim 1, wherein said at least one of the first and second tube holders comprises a pair of clamps retaining the separable pieces of said holding portion.

4. A tube connecting apparatus according to claim 1, wherein each of said first tube holder and said second tube holder is arranged so that said first tube holder and said second tube holder are movable toward and away from each other.

5. A tube connecting apparatus according to claim 1, wherein said cutting means is movable between said first tube holder and said second tube holder.

* * * * *